United States Patent
Tominaga et al.

(10) Patent No.: US 6,320,192 B1
(45) Date of Patent: Nov. 20, 2001

(54) DETECTOR FOR USE IN INFRARED ANALYZER, FLOW DETECTOR AND MANUFACTURING METHOD THEREOF

(75) Inventors: Koji Tominaga; Koichi Matsumoto; Shuji Takada, all of Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/321,733

(22) Filed: May 28, 1999

(30) Foreign Application Priority Data

May 29, 1998 (JP) .................................................. 10-166418
Jun. 26, 1998 (JP) .................................................. 10-181172

(51) Int. Cl.$^7$ ................................................. G01N 21/26
(52) U.S. Cl. ........................................... 250/344; 250/343
(58) Field of Search ..................................... 250/344, 343

(56) References Cited

U.S. PATENT DOCUMENTS

| | | | | |
|---|---|---|---|---|
| 4,103,163 | * | 7/1978 | Hamada ................................. | 250/344 |
| 5,572,031 | * | 11/1996 | Cooper et al. ........................ | 250/343 |
| 5,764,354 | * | 6/1998 | Aidam et al. ......................... | 250/343 |
| 5,886,348 | * | 3/1999 | Lessure et al. ....................... | 250/343 |

\* cited by examiner

Primary Examiner—Constantine Hannaher
Assistant Examiner—Andrew Israel
(74) Attorney, Agent, or Firm—Sughrue, Mion, Zinn, Macpeak & Seas, PLLC

(57) ABSTRACT

A detector 1 for use in infrared gas analyzers has two compartments 14 and 15 to be filled with gas G showing the same absorption characteristics as the gas to be measured and which are arranged in series with a load cell 2, and the gas compartments 14 and 15 communicate with each other via a gas channel 16 in which a pyroelectric flow detector element 19 is provided. Pyroelectric flow detector element B is produced by a process which includes the steps of forming a lower electrode 111 on a substrate 112, forming a thin ferroelectric film 109 on the lower electrode, forming an upper electrode 110 on the thin ferroelectric film, patterning the upper electrode, the thin ferroelectric film and the lower electrode in that order by photolithography, with gas passage holes 115 being also formed, thereafter forming a thin insulator film 113 that covers a pyroelectric sensing portion 108 that is composed of the upper electrode, the thin ferroelectric film and the lower electrode, with gas passage holes and contact holes 117 and 118 being also formed in said thin insulator film, forming a heating electrode film on the thin insulator film, patterning the heating electrode film by photolithography, allowing a portion of the heating electrode film to drop in the contact holes to make lead-ins for the upper and lower electrodes, and etching away that part of the substrate which is just under the pyroelectric sensing portion to form an opening 112a.

12 Claims, 22 Drawing Sheets

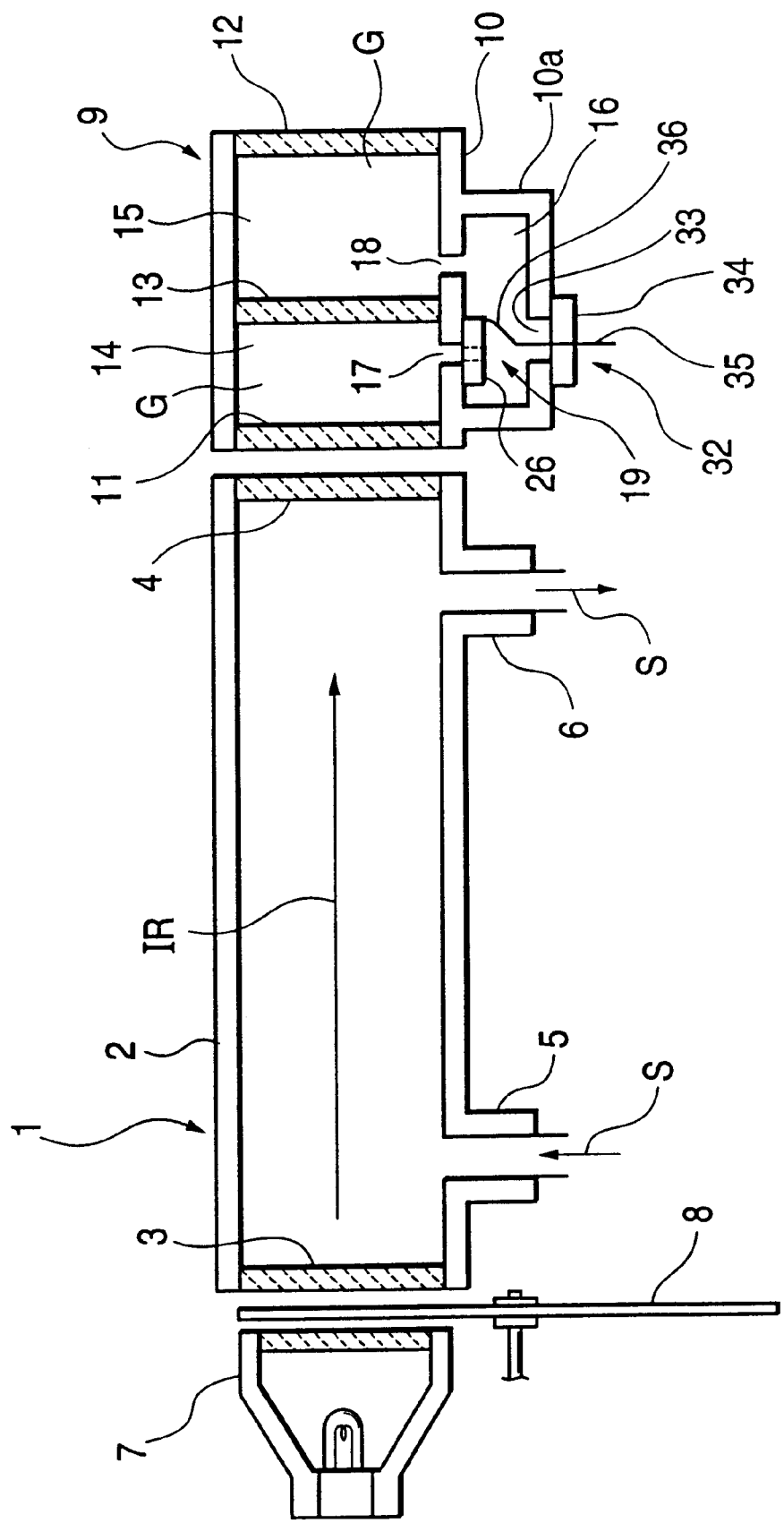

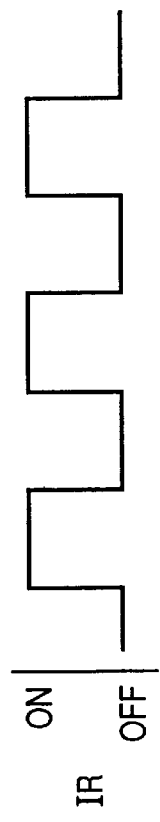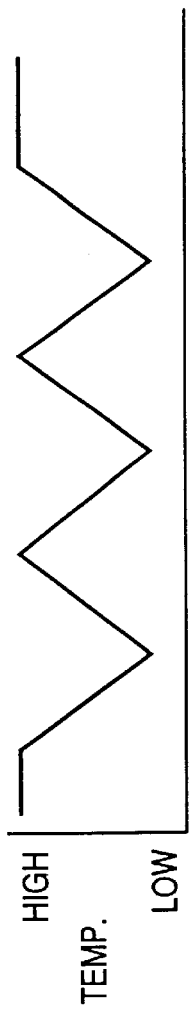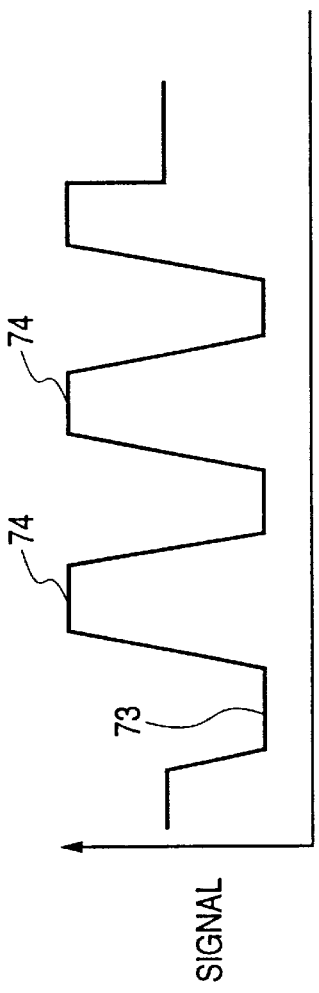

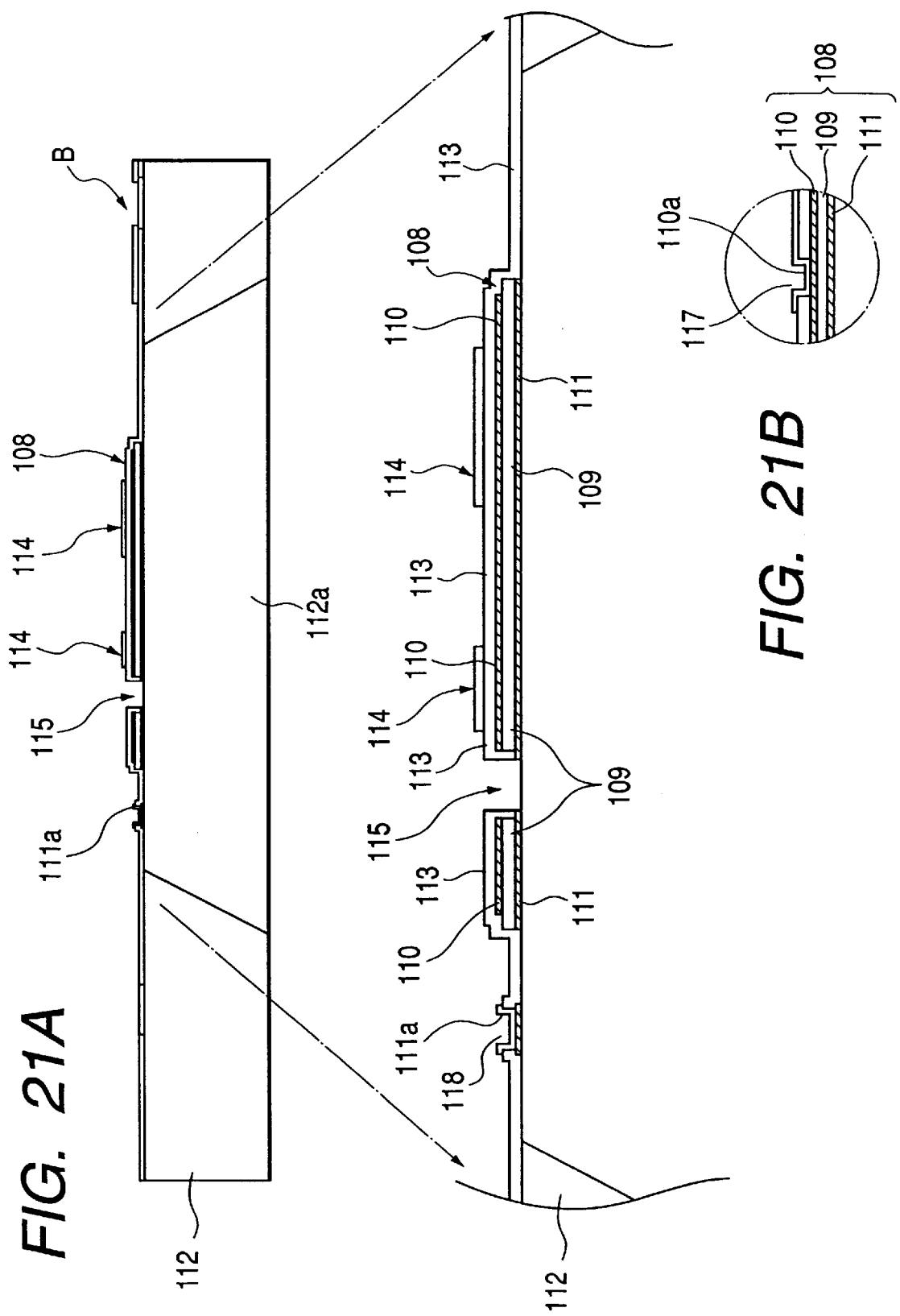

DETECTOR FOR USE IN INFRARED ANALYZER, FLOW DETECTOR AND MANUFACTURING METHOD THEREOF

BACKGROUND OF THE INVENTION

This invention relates to a detector for use in so-called "nondispersive infrared gas analyzer" (NDIR), a flow detector element for use in the detector, and a process for producing the element.

A detector for use in infrared gas analyzers is known that comprises two gas compartments that are filled with a gas showing the same absorption characteristics as the gas to be measured and that are arranged in series with or parallel to a load cell, a gas channel via which the two gas compartments communicate with each other, and a flow detector element provided in said gas channel in a position that blocks it. The flow detector element may be of a thermal type as described in Examined Published Japanese Utility Model Publication (kokoku) Nos. 59-26278/(1984) and 59-24993/(1984), as well as Unexamined Published Japanese Utility Model Application (kokai) No. 56-99462/(1981) and Unexamined Published Japanese Patent Application No. 7-140075/(1995).

As shown in FIGS. 1 and 2, the thermal flow detector element consists of two heaters (a) that are made of a metal (e.g. Ni) foil and that run in a serpentine path and plates (b) that are made of an insulating material such as glass and which support the two heaters (a) in a face-to-face relationship. The plates (b) have an opening (c) and the gaps (d) between adjacent branches of each heater (a) that are located within the opening (c) provide gas flow channels.

With a constant voltage being applied to the heaters (a) so that their temperature becomes higher than that of the gas in the gas compartments by a certain value, the two heaters a provide the temperature profile shown by (i) in FIG. 2 if there is no gas flow. However, if the gas flows through the gaps d as indicated by an arrow, the heater (a) in the upstream position is cooled in accordance with the gas flow rate whereas the heater (a) in the downstream position is heated with the heat taken from the upstream heater (a); as the result, the two heaters (a) provide the temperature profile shown by (j) in FIG. 2. This temperature change causes a change in the resistance of the heaters (a), which is measured with a Wheatstone bridge, thereby detecting the gas flow. Note that the detected gas flow corresponds to the quantity of infrared absorption by the gas of interest (hence its concentration) that is passed through the load cell (not shown) in a nondispersive infrared gas analyzer.

However, the above-described conventional detector has several limitations. First, the resistance of the metal of which the heaters are made does not have a very high temperature coefficient. Second, the heaters cannot be supplied with a very high voltage.

Thirdly, the heating temperature cannot be very high and if it approaches 500° C., the gas in the gas compartments will deteriorate or decompose. Because of these difficulties, the signal output is very small and the detection sensitivity is accordingly low and dependent on the ambient temperature.

According to Unexamined Published Japanese Patent Application (kokai) No. 60-173443/(1985), it is proposed that a pressure detector be used in place of the detector element working as a thermal flow meter. A problem with this proposal is that due to the need to detect a small pressure difference, a large enough signal output cannot be produced to achieve high detection sensitivity.

The conventional thermal flow detector element shown in FIGS. 1 and 2 has the following additional problems. Since all gaps (d) between adjacent branches of each heater (a) that are located within the opening (c) serve as gas flow channels, the channel or flow path area is large compared to the area of the detector element and the gas flow rate is so much retarded that the change in the temperature of the heaters (a) due to the gas flow is insufficient to provide high sensitivity.

That part of the heaters a which is located within the opening (c) (i.e., which is not supported with the plates (b)) must have a sufficient strength to retain shape, so a thick enough metal foil has to be used to compose the heaters (a). However, if the thickness of the heaters (a) is increased, the heat capacity increases correspondingly to slow down the response speed.

SUMMARY OF THE INVENTION

The present invention has been accomplished under these circumstances and has as an objective providing a detector for use in infrared gas analyzers that has a markedly higher sensitivity than the prior art version and which yet is not subject to the effects of disturbances such as ambient temperature.

Another object of the invention is to increase the sensitivity and response speed of a flow detector element for use in infrared gas analyzers.

The first object of the invention can be attained by a detector for use in infrared gas analyzers that has two gas compartments to be filled with a gas showing the same absorption characteristics as the gas to be measured and which are arranged in series with a load cell, characterized in that said gas compartments communicate with each other via a gas channel in which a pyroelectric flow detector element is provided.

The two gas compartments may be arranged in parallel so that they correspond to the load cell and a reference cell, respectively. If desired, the sensing portion of the pyroelectric flow detector element may be adapted to be heatable.

The first object of the invention can also be attained by a detector for use in infrared gas analyzers that has two gas compartments to be filled with a gas showing the same absorption characteristics as the gas to be measured and which are arranged in series with a load cell, characterized in that said gas compartments communicate with each other via a gas channel in which a first pyroelectric flow detector element is provided, with a second pyroelectric flow detector element being provided as a compensating means in the neighborhood of said first pyroelectric flow detector element.

The two gas compartments may be arranged in parallel so that they correspond to the load cell and a reference cell, respectively.

The first object of the invention can also be attained by a detector for use in infrared gas analyzers that has two gas compartments to be filled with a gas showing the same absorption characteristics as the gas to be measured and which are arranged in series with a load cell, characterized in that said gas compartments communicate with each other via a gas channel in which two pyroelectric flow detector elements are provided in a superposed relationship.

The two gas compartments may be arranged in parallel so that they correspond to the load cell and a reference cell, respectively.

At least one of the pyroelectric flow detector elements may be adapted to be heatable.

The above-described detector for use in infrared gas analyzers employs one or two pyroelectric flow detector elements and, hence, is capable of positive detection of the slightest change in the gas temperature to produce a sufficiently large signal output that its sensitivity is significantly improved over that of the conventional detector for use in infrared gas analyzers.

The second object of the invention can be attained by a flow detector element in a detector for use in infrared gas analyzers that comprises two gas compartments filled with a gas showing the same absorption characteristics as the gas to be measured, a gas channel via which the two gas compartments communicate with other, and a flow detector element provided in said gas channel in a position that blocks it, characterized in that a gas passage hole whose setting of channel area is smaller than the area of the gap between adjacent segments of a heater to be supplied with a constant voltage s o that its temperature is a certain value higher than the temperature of the gas in the gas compartments is formed in the neighborhood of said heater.

The flow detector element may be of either a thermal or pyroelectric type.

Since gas passage holes of which the channel area is smaller than the area of the gap between adjacent segments of the heater to be supplied with a constant voltage are provided near the heater, the flow rate of the gas flowing through the gas passage holes is sufficiently increased that the temperature of the heater experiences a great enough change to provide a higher sensitivity.

According to the other aspect of the invention, there if provided a process for producing a flow detector element for use in infrared gas analyzers, which comprises the steps of depositing a thin insulator film on a substrate, forming gas passage holes in said thin insulator film, forming a heating electrode film on said thin insulator film and removing part of the substrate to form an opening, thereby making a unit of detector element, and bonding two such units of detector element in superposition to produce a thermal flow detector element.

There is also provided a process for producing a flow detector element for use in infrared gas analyzers, which comprises the steps of forming a lower electrode on a substrate, forming a thin ferroelectric film on the lower electrode, forming an upper electrode on the thin ferroelectric film, patterning the upper electrode, the thin ferroelectric film and the lower electrode in that order, with a gas passage through-hole being also formed, thereafter forming a thin insulator film that covers a pyroelectric sensing portion that is composed of the upper electrode, the thin ferroelectric film and the lower electrode, with a through-hole and contact holes being also formed in said thin insulator film, forming a heating electrode film on the thin insulator film, allowing a portion of the heating electrode film to drop in the contact holes to make lead-ins for the upper and lower electrodes, and removing that part of the substrate which is just under the pyroelectric sensing portion to form an opening, thereby producing a pyroelectric flow detector element.

According to the processes described above, gas passage holes can be formed without regard to the conductor size and pattern of the heater and by reducing the channel area of the gas passage holes, the gas flow rate can be sufficiently increased to provide higher sensitivity. In addition, the heater is supported by the thin insulator film, so there is no need to use a thick heating electrode film and both thermal and pyroelectric flow detector elements can be formed as thin enough films to reduce the heat capacity and thereby increase the response speed. A particular advantage results from the pyroelectric flow detector element which theoretically can produce by far greater signal outputs than the thermal type to achieve a marked improvement in detection sensitivity.

BRIEF DESCRIPTION OF THE PREFERRED EMBODIMENTS

FIG. 3 is a schematic representation of a gas analyzer of single-beam type incorporating the detector of the invention;

FIG. 13A shows how an infrared beam is launched into the detector shown in FIG. 3 when it is heated with a heater:

FIG. 13B shows the temperature profile of a pyroelectric flow detector element;

FIG. 13C shows how output signals are produced from the detector shown in FIG. 3 when it is heated with a heater;

FIG. 21A is section Y—Y of FIG. 20;

FIG. 21B is a partial enlarged section of FIG. 20;

DETAILED DESCRIPTION OF THE PREFERRED EMBODIMENTS

Figure 1:
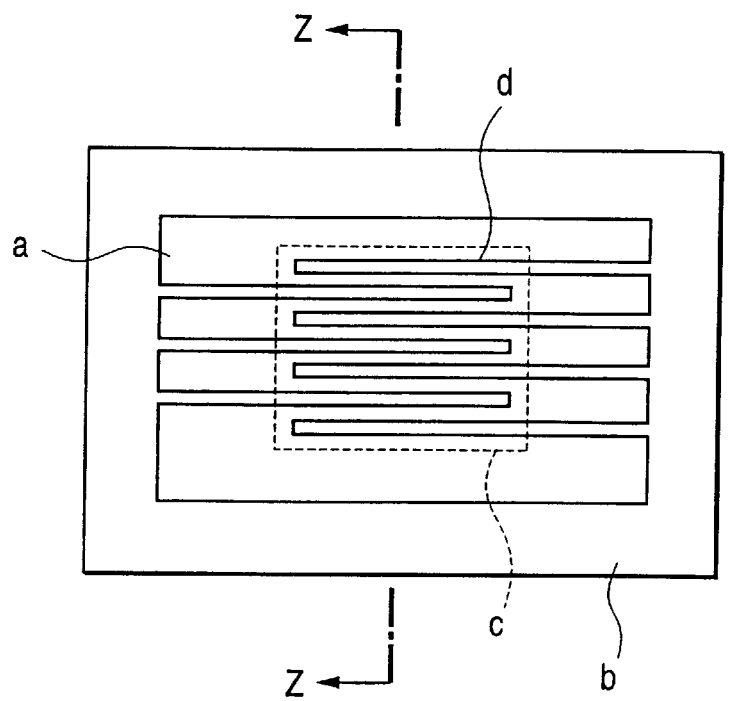
FIG. 1 is a plan view of a conventional thermal flow detector element.

Several embodiments of the invention will now be described with reference to accompanying drawings. FIG. 3 is a schematic representation of a gas analyzer 1 incorporating the detector of the invention for use in infrared gas analyzers (which is hereinafter referred to simply as "detector"). The infrared gas analyzer 1 shown in FIG. 3 is according to the first embodiment of the invention and is of a so-called "single-beam type".

The infrared gas analyzer 1 is composed as shown in FIG. 3. A tubular load cell 2 is sealed at opposite ends with cell windows 3 and 4 each of which is made of an infrared transmitting material. A sample gas S is admitted into the cell 2 through an inlet 5 and emerges from it through an outlet 6. An infrared source 7 is provided to face the cell window 3. An infrared beam (IR) issuing from the infrared source 7 is interrupted at a specified frequency with a light chopper 8 that is interposed between the infrared source 7 and the cell window 3 and which is driven to rotate with a motor (not shown).

A detector 9 is provided to face the other cell window 4 and its housing 10 is sealed at opposite ends with windows 11 and 12 each of which is made of an infrared transmitting material. The interior of the detector 9 is divided into two gas compartments 14 and 15 by a window 13 made of an infrared transmitting material. The two gas compartments 14 and 15 are arranged in series with the infrared optical path (indicated by arrow IR) through the load cell 2. The gas compartments 14 and 15 are each filled with a gas G that shows the same absorption characteristics as the gas to be measured (if desired, these compartments may be filled with the gas to be measured). The detector 9 in the first embodiment is adapted to be such that the infrared beam is absorbed in both gas compartments 14 and 15. If desired, the infrared beam may be absorbed in the compartment 14 only and if this is the case, the two gas compartments 14 and 15 are separated by a wall made of an infrared opaque material.

The gas compartments 14 and 15 communicate with each other via a gas channel 16; in the first embodiment, the gas channel 16 is formed outside the housing 10 as the result of it being defined by the housing 10 and a sidewall 10a which is an integral part thereof. The gas channel 16 is open to the gas compartments 14 and 15 via openings 17 and 18, respectively. In the illustrated case, the gas channel 16 has a pyroelectric flow detector element 19 provided at the opening 17. The pyroelectric flow detector is a type of differential sensor, and outputs a signal responsive to a change of temperature.

Figure 4A:
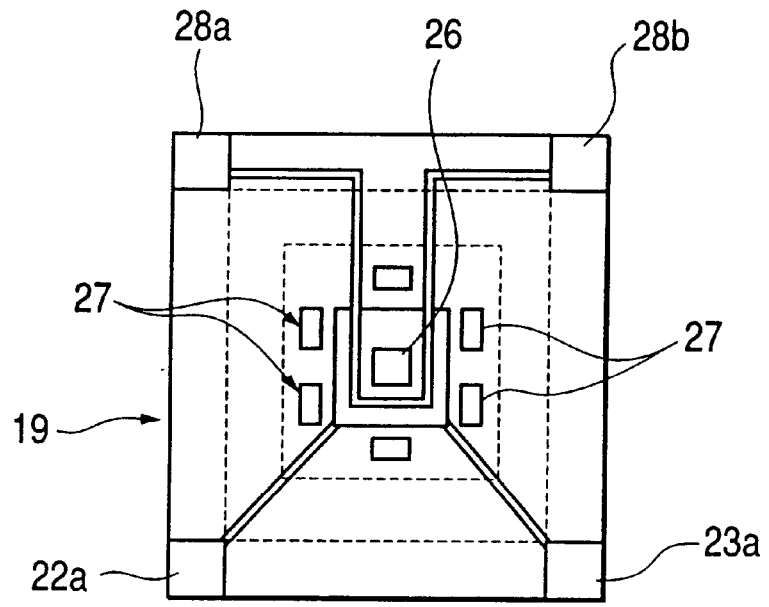
FIG. 4A is a plan view showing schematically an exemplary pyroelectric flow detector element which is to be incorporated in the detector of the invention.
Figure 4B:
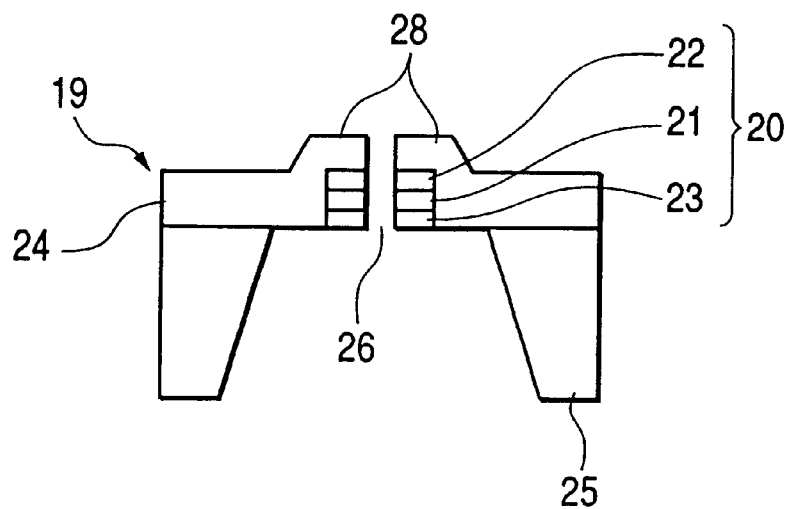
FIG. 4B is a longitudinal section of FIG. 4A.
Figure 5A:
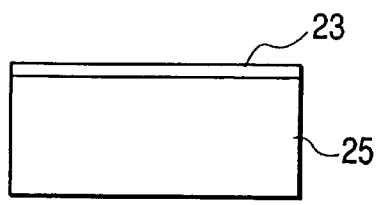
FIGS. 5A to 5G show the sequence of steps in an exemplary process for producing the pyroelectric flow detector element shown in FIG. 4.
Figure 5B:
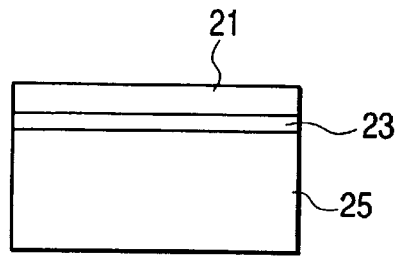
Figure 5C:
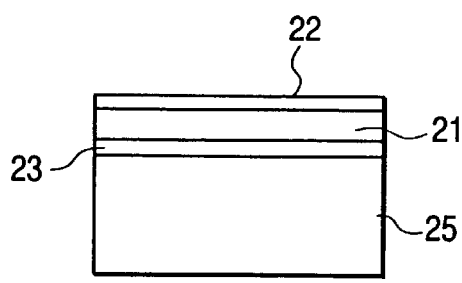
Figure 5D:
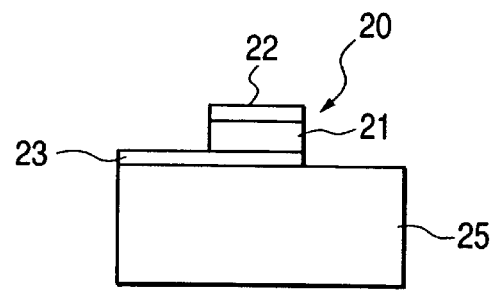
Figure 5E:
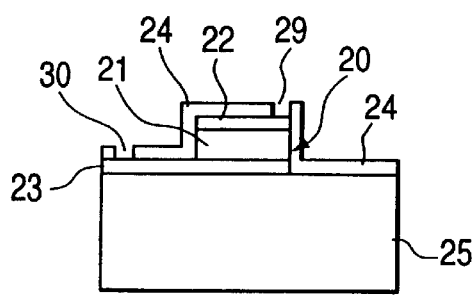
Figure 5F:
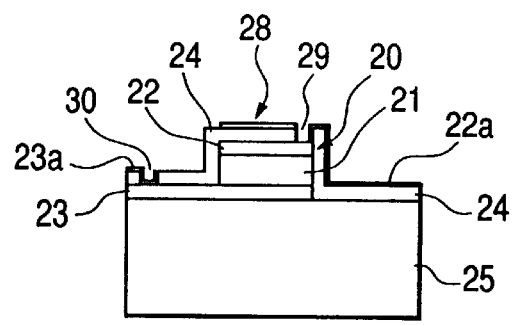
Figure 5G:
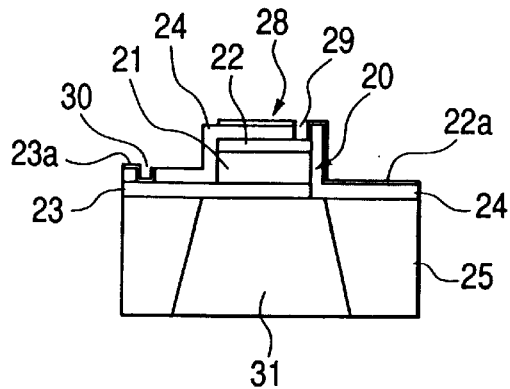
Figure 6:
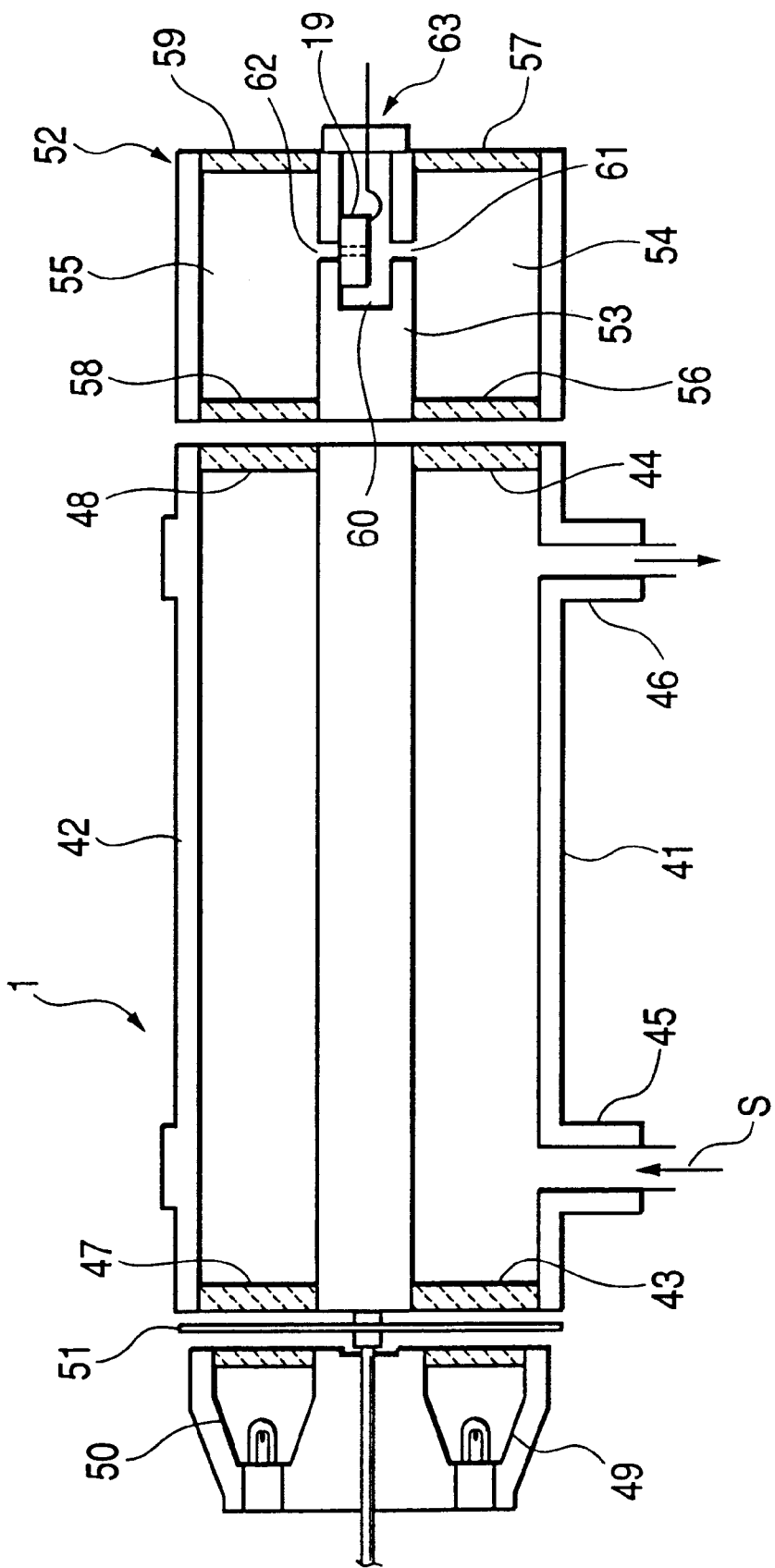
FIG. 6 is a schematic representation of a gas analyzer of double-beam type incorporating the detector of the invention.

FIGS. 4A and 4B show schematically the construction of the pyroelectric flow detector element 19. Shown by 20 is a pyroelectric sensing portion that consists of a thin pyroelectric film 21, an upper electrode 22 that is formed on top of the thin pyroelectric film 21, and a lower electrode 23 that is formed under the pyroelectric film 21. The pyroelectric sensing portion 20 is supported on a substrate 25 with a thin insulator film 24 being interposed. The thin insulator film 24 may be formed of organic matter such as a polyimide or inorganic matter such as $SiO_2$ or $Si_4N_3$; insulators having lower heat conductivities than metals are preferred. A gas passage through-hole 26 is formed in the center of the pyroelectric sensing portion 20. A plurality of through-holes 27 formed around the pyroelectric sensing portion 20 may also be used as gas passage holes. A heater 28 is provided on top of the upper electrode 22 with the thin insulator film 24 interposed. Indicated by 22a is a lead-in for the upper electrode 22 and 23a is a lead-in for the lower electrode 23. The heater 28 also has lead-ins 28a and 28b.

We now describe an exemplary process for producing the pyroelectric flow detector element 19 with reference to FIGS. 5A to 5G. A substrate 25 which is made of single-crystal MgO or Si is sputtered or otherwise treated to be overlaid with a Pt layer in a thickness of about 0.2 $\mu$m so that it works as the lower electrode 23 (see FIG. 5A). The lower electrode 23 is treated by MOCVD (metalorganic chemical vapor deposition) or otherwise to be overlaid with a thin PZT or PLZT ferroelectric film 21 in a thickness of about 2 to 5 $\mu$m (see FIG. 5B). The thin ferroelectric film 21 is sputtered or otherwise treated to be overlaid with a Au or Pt layer in a thickness of about 0.2 $\mu$m so that it works as the upper electrode 22 (see FIG. 5C). The upper electrode 22, the thin ferroelectric film 21 and the lower electrode 23 (which combine to form the pyroelectric sensing portion 20) are sequentially patterned by photolithography (see FIG. 5D). The patterning is performed with an etching hole (not shown) being also formed, which later serves as a gas passage hole.

The pyroelectric sensing portion 20 is covered with a thin insulator film 24. The thin insulator film 24 has an etching hole (not shown) which later serves as a gas passage hole and contact holes 29 and 30 (see FIG. 5E). The thin insulator film 21 is overlaid with a heating electrode film (typically from Pt or NiCr) that later serves as a heater 28. The heating electrode film is then patterned by photolithography, with Pt or NiCr being allowed to drop in the contact holes 29 and 30 so as to form lead-ins 22a and 23a for the upper electrode 22 and the lower electrode 23, respectively (see FIG. 5F). That part of the substrate 25 which is just under the pyroelectric sensing portion 20 is etched away (see FIG. 5G). The etching may be performed either from the top or the bottom of the substrate 25. If it is performed from the top, phosphoric acid in solution at a specified temperature may be injected as a liquid etchant through the etching hole. Indicated by 31 in FIG. 5G. is the removed portion of the substrate.

Note that the pyroelectric flow detector element 19 has already been proposed in Unexamined Published Japanese Patent Application (kokai) No. 10-197550/(1998).

Referring back to FIG. 3, the thus constructed pyroelectric flow detector element 19 is fitted gastightly such that excepting the through-hole 26 made in the center of the pyroelectric sensing portion 20, said element 19 seals the opening 17 through which the gas channel 16 is open to the gas compartment 14. More specifically, the pyroelectric flow detector element 19 is fitted with the central axis of the through-hole 26 being in registry with the central axis of the opening 17, so that the gas compartment 14 communicates with the gas channel 16 only by way of the opening 17 and the through-hole 26.

Shown by 32 in FIG. 3 is a signal pick-up portion formed in the sidewall 10a which defines the gas channel 16 together with the housing 10. An opening 33 is made in the sidewall 10a and closed with a detachable lid 34. A plurality of lead pins 35 penetrate through the lid 34 in a gastight manner. The lead pins 35, the pyroelectric flow detector element 19 and a signal output portion (not shown) are electrically connected with lead wires 36. At the other end, the lead pins 35 are connected to a signal processing portion (not shown).

Let us now describe the operation of the detector 9 constructed in the way shown in FIG. 3. Suppose first that the gas compartments 14 and 15 in the detector 9 are filled with the same gas to be measured. When the infrared beam IR is launched into the detector 9 as shown in FIG. 3, the gas compartment 14 is the first to receive the infrared beam IR. The gas G in the gas compartment 14 absorbs a portion of the infrared beam IR to become heated and expand. The expanded gas G passes through the opening 17, the through-hole 26 in the pyroelectric flow detector element 19 the gas channel 16 and the opening 18 in that order to flow into the gas compartment 15. Due to the rising temperature of the gas G, a temperature difference occurs in the pyroelectric sensing portion 20 of the pyroelectric flow detector element 19 and the sensing portion 20 outputs a signal corresponding to said temperature difference.

In the first embodiment described above, the infrared gas analyzer 1 is of a so-called "single-beam type" but this is not the sole case of the invention and the infrared gas analyzer 1 may be constructed as a so-called "double-beam type" in which two cells are placed side by side. This type or infrared gas analyzer is hereunder described as the second embodiment of the invention.

Indicated by 41 and 42 are a load cell and a reference cell, respectively, that are tubular in shape and placed side by side. The load cell 41 is sealed at opposite ends with cell windows 43 and 44 each of which is made of an infrared transmitting material. A sample gas S is admitted into the cell 2 through an inlet 45 and emerges from it through an outlet 46. The reference cell 42 is also sealed at opposite ends with infrared transmitting cell windows 47 and 48 each of which is made of an infrared transmitting material. The reference cell is filled with a zero gas (e.g., nitrogen gas) which does not absorb an infrared beam IR.

An infrared source 49 (or 50) is provided to face the cell window 43 (or 47) of the load cell 41 (or reference cell 42). An infrared beam IR issuing from the infrared source 49 (or 50) is interrupted at a specified frequency with a light chopper 51 that is interposed between the infrared source 49 (or 50) and the cell window 43 (or 47) and which is driven to rotate with a motor (not shown).

A detector 52 is provided to face the other cell windows 44 and 48 and its interior is divided into two compartments 54 and 55 by a partition 53 that correspond to the load cell 41 and the reference cell 42, respectively. The compartment 54 (or 55) is sealed at opposite ends with windows 56 and 57 (or 58 and 59) that are made of an infrared transmitting material. The gas compartments 54 and 55 are each filled with a gas G that shows the same absorption characteristics as the gas to be measured (if desired, these gas compartments may be filled with the gas to be measured).

The gas compartments 54 and 55 communicate with each other via a gas channel 60; in the first embodiment, the gas channel 60 is formed within the partition 53. The gas channel 60 is open to the gas compartments 54 and 55 via openings 61 and 62, respectively. In the illustrated case, the gas channel 60 has a pyroelectric flow detector element 19 provided at the opening 62. Indicated by 63 is a signal pickup portion that is constructed in the same as the signal pickup portion 32 in the first embodiment and which, hence, need not be described in detail.

The operation of the detector 52 in the second embodiment operates is the same as that of the detector 9 in the first embodiment and need not be described in detail.

In the first and second embodiments, the detector 9 or 52 has only one pyroelectric flow element 19. If desired, the detector may have two pyroelectric flow elements 19 and 19' of the same construction. The two pyroelectric flow detector elements 19 and 19' may be stacked one on top of the other or placed side by side. The former case is hereunder described as the third embodiment of the invention and the latter as the fourth embodiment. In the following description, the components of the pyroelectric flow detector element 19' are marked with a prime.

Figure 7A:
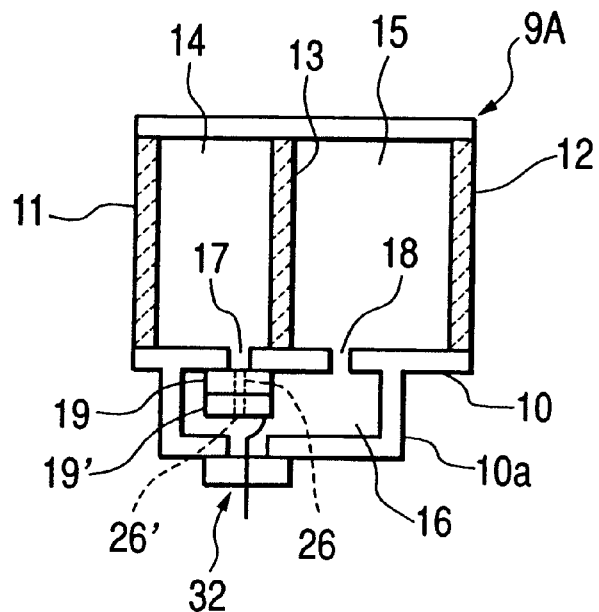
FIG. 7A is a sectional view showing another composition of the detector of the invention which is to be used in a single-beam type gas analyzer.
Figure 7B:
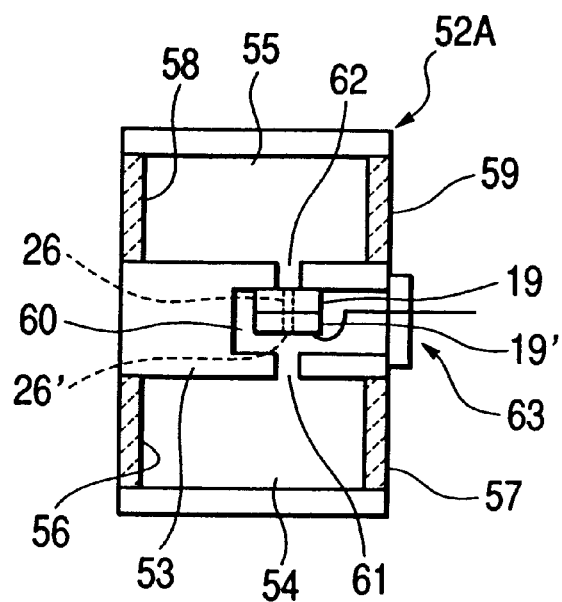
FIG. 7B is a sectional view showing yet another composition of the detector of the invention which is to be used in a double-beam type gas analyzer.

FIGS. 7A and 7B show the third embodiment. In FIG. 7A, a detector 9A adaptive to a single beam has one pyroelectric flow detector element 19 provided in the gas channel 16 with the through-hole 26 being in registry with the opening 17. In addition, the other pyroelectric flow detector element 19' having an identical construction to the pyroelectric flow detector element 19 (which therefore has the same values of thermal time constant and sensitivity) is stacked on the element 19. As shown by an equivalent circuit in FIG. 9A or 9B, electrodes of the same polarity (upper electrodes 22 and 22' or lower electrodes 23 and 23') are connected together.

FIG. 7B shows a detector 52A adaptive to a double beam which has the pyroelectric flow detector element 19 provided in the channel 16 with the through-hole 26 being in registry with the opening 17. In addition, the other pyroelectric flow detector element 19' having an identical construction to the pyroelectric flow detector element 19 is stacked on the element 19. As shown by an equivalent circuit in FIG. 9A or 9B, electrodes of the same polarity are connected together.

As will be described later in detail, the third embodiment of the invention enables both pyroelectric flow detector elements 19 and 19' to perform flow measurement, producing greater signals than when the pyroelectric flow detector element 19 alone is provided.

Figure 8A:
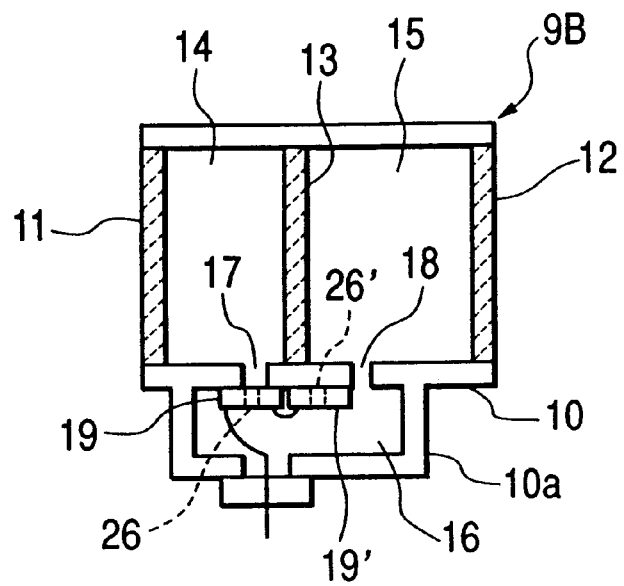
FIG. 8A is a sectional view showing another composition of the detector of the invention which is to be used in a single-beam type gas analyzer.
Figure 8B:
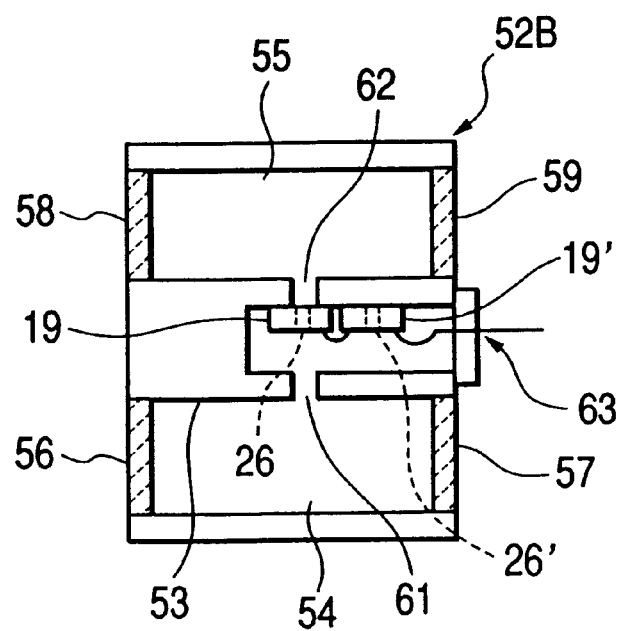
FIG. 8B is a sectional view showing yet another composition of the detector of the invention which is to be used in a double-beam type gas analyzer.

FIGS. 8A and 8B show the fourth embodiment of the invention. In FIG. 8A, a detector 9B adaptive to a single beam has the pyroelectric flow detector element 19 provided in the gas channel 16 with the through-hole 26 being in registry with the opening 17. In addition, the other pyroelectric flow detector element 19' having an identical construction to the pyroelectric flow detector element 19 is placed adjacent the element 19.

FIG. 8B shows a detector 52B adaptive to a double beam which has the pyroelectric flow detector element 19 provided in the gas channel 16 with the through-hole 26 being in registry with the opening 17. In addition, the other pyroelectric flow detector element 19' having an identical construction to the pyroelectric flow detector element 19 is placed adjacent the element 19.

Figure 9A:
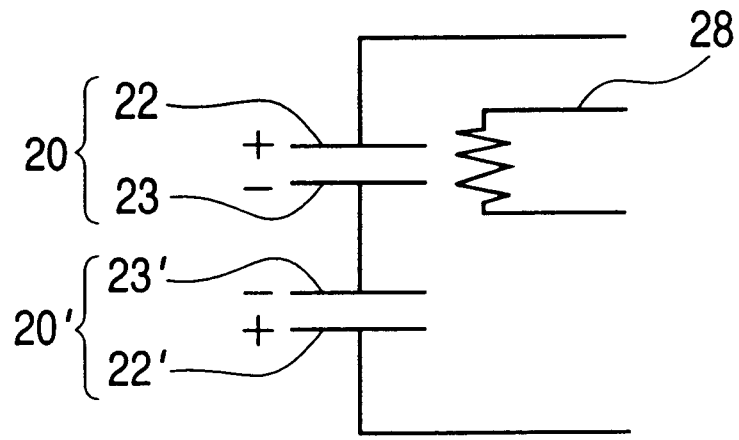
FIGS. 9A and 9B are equivalent circuits of the detectors shown in FIGS. 7 and 8.
Figure 9B:
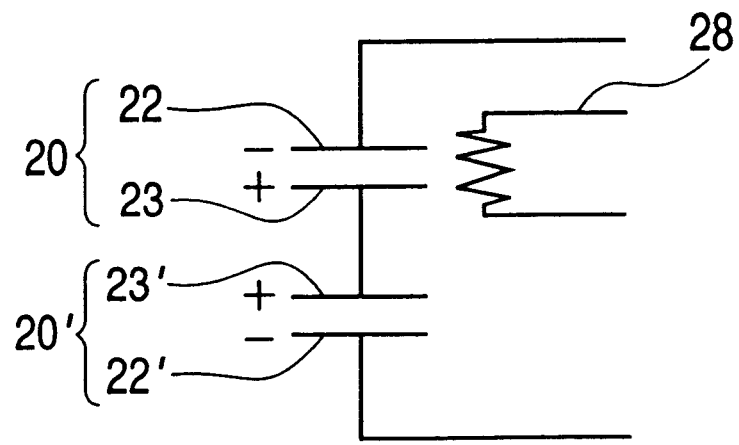
Figure 10A:
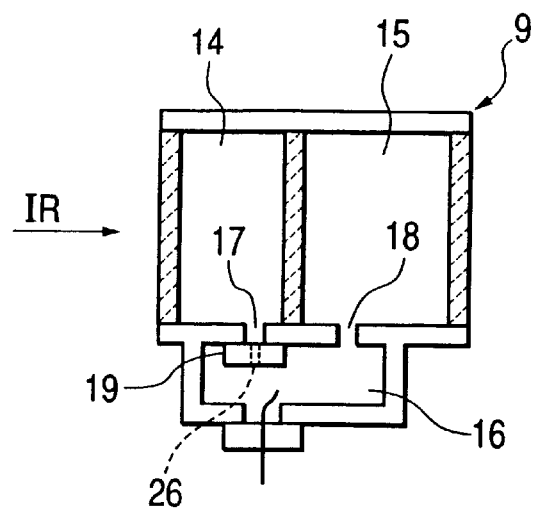
FIGS. 10A to 10C show in sequence how the detector shown in FIG. 3 operates when it is not heated with a heater.
Figure 10B:
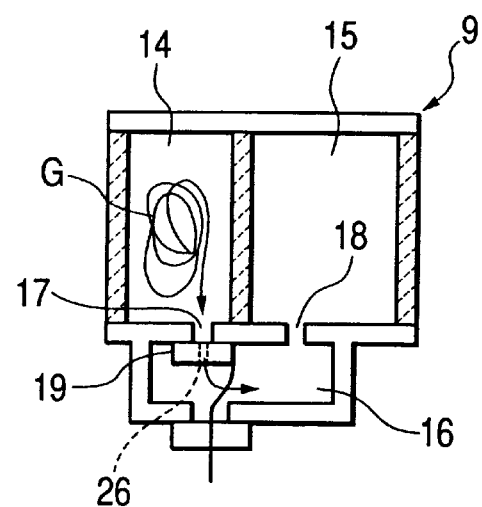
Figure 10C:
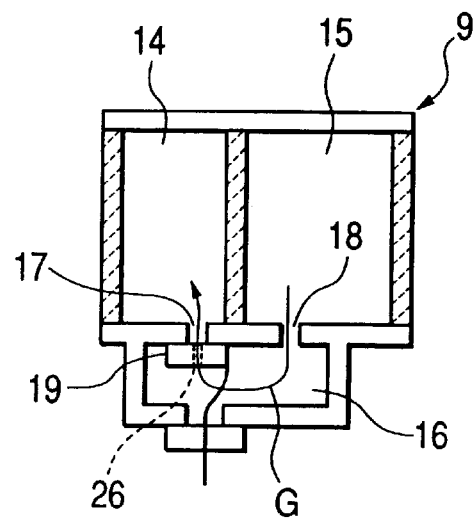

As shown by an equivalent circuit in FIG. 9A or 9B, the fourth embodiment parallels with the third embodiment in that electrodes of the same polarity (upper electrodes 22 and 22' or lower electrodes 23 and 23') are connected together.

As will be described later in detail, the fourth embodiment is characterized in that of the two pyroelectric flow detector elements 19 and 19', the first mentioned element 19 is responsible for flow measurement whereas the other element 19' is responsible for temperature compensation. Hence, the fourth element enables temperature-compensated measurement.

Of the four embodiments described above, the detector 9 shown in FIG. 3 and the detector 9A shown in FIG. 7A are discussed below with reference to FIGS. 10A to 15F.

Figure 11A:
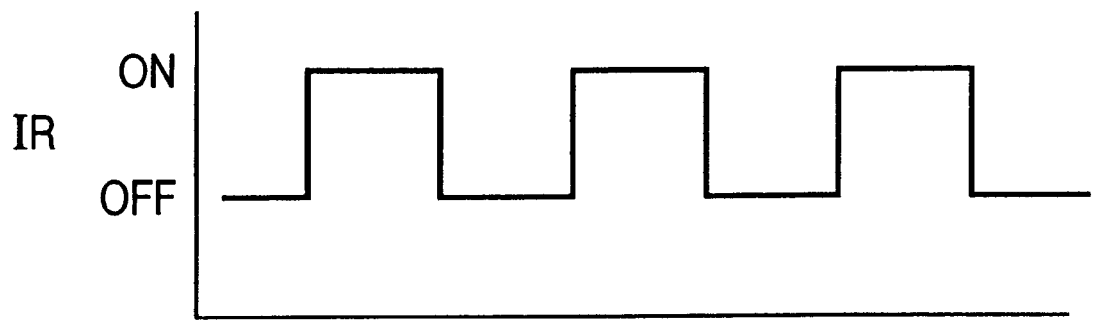
FIG. 11A shows how an infrared beam is launched into the detector shown in FIG. 3 when it is not heated with a heater.
Figure 11B:
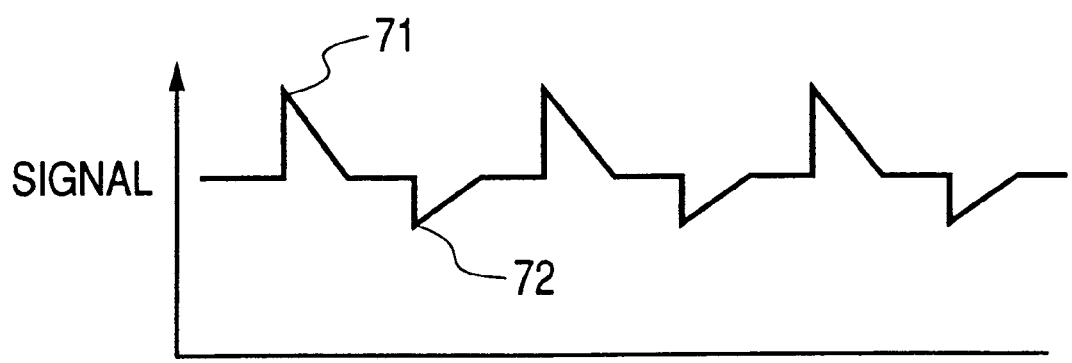
FIG. 11B shows how output signals are produced from the detector shown in FIG. 3 when it is not heated with a heater.

I. First consider the case where the heater 28 (see FIG. 4) in the detector 9 shown in FIG. 3 is off. The following discussion should be read with reference to FIGS. 10A to 10C, as well as FIGS. 11A and 11B. FIG. 11A shows how the admission of an infrared beam IR into the detector 9 is interrupted (turned on and off), and FIG. 11B shows signals that are correspondingly output from the pyroelectric flow detector element 19.

In the assumed case, the pyroelectric flow detector element 19 has the same temperature as the housing of the detector. Suppose first that an infrared beam IR is launched into the gas compartments 14 and 15 through the infrared transmitting window 11 (see FIG. 10A). since the gas compartment 14 is the first to receive the admitted infrared beam IR, the gas in that compartment absorbs the infrared beam IR to become heated. However, the gas in the compartment 15 is little heated since the infrared beam IR has been absorbed by the gas in the compartment 14.

The heated gas G in the gas compartment 14 expands (see FIG. 10B) and passes through the opening 17 and the through-hole 26 in the pyroelectric flow detector element 19 (hereinafter the word "through-hole 26" is assumed in the expression of "passage through the pyroelectric flow detector element 19") to enter the gas channel 16, from which it passes through the opening 18 to flow into the gas compartment 15. In this process, the heated gas raises the temperature of the pyroelectric flow detector element 19 and signals indicative of the resulting temperature change are output as indicated by a reference numeral 71 in FIG. 11B.

When the infrared beam IR is no longer admitted into the gas compartments 14 and 15, the gas G is thermally in equilibrium; hence, the gas G that has flowed out of the gas compartment 14 into the gas compartment 15 moves backward, passing through the opening 18, gas channel 16, pyroelectric flow detector element 19 and opening 17 to return into the gas compartment 14. In this process, the once heated pyroelectric flow detector element 19 cools down and its temperature becomes equal to that of the housing of the detector, producing signals that are output as indicated by a reference numeral 72 in FIG. 11B. Note that the temperature change occurring in the process is not abrupt and the output signals are not very large.

II. We then consider the case where the heater 28 in the detector 9 shown in FIG. 3 is turned on to hold the pyroelectric flow detector element 19 at a constant temperature. The following discussion should be read with reference to FIGS. 12A to 12C and FIGS. 13A to 13C. FIG. 13A shows how an infrared beam IR is interrupted (turned on and off); FIG. 13B shows the temperature change in the pyroelectric flow detector element 19; and FIG. 13C shows signals that are correspondingly output from the pyroelectric flow detector element 19.

Figure 12A:
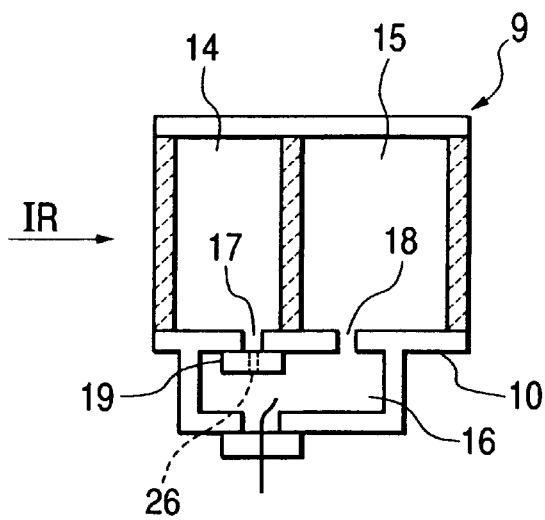
FIGS. 12A to 12C show in sequence how the detector shown in FIG. 3 operates when it is heated with a heater.
Figure 12B:
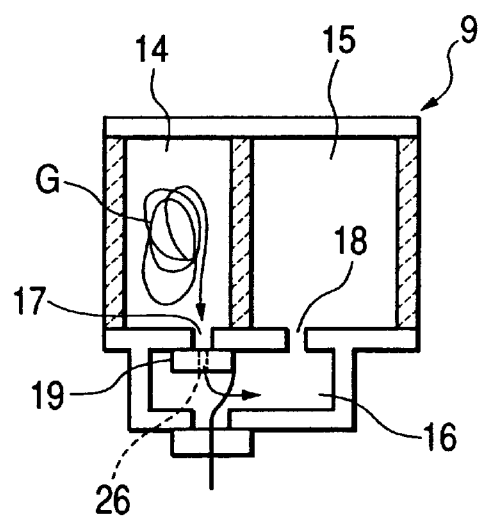
Figure 12C:
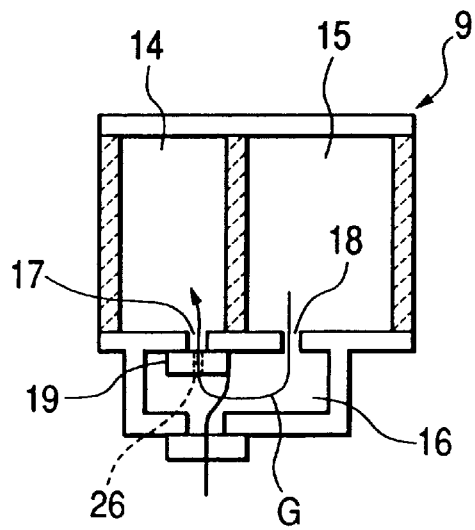

Suppose first that with the pyroelectric flow detector element 19 being held at a specified temperature, an infrared beam IR is launched into the gas compartments 14 and 15 through the infrared transmitting window 11 (see FIG. 12A). Since the gas compartment 14 is the first to receive the admitted infrared beam IR, the gas in that compartment absorbs the infrared beam IR to become heated. However, the gas in the compartment 15 is little heated since the infrared beam IR has been absorbed by the gas in the compartment 14.

The heated gas G in the gas compartment 14 expands (see FIG. 12B) and passes through the opening 17 and the pyroelectric flow detector element 19 to enter the gas channel 16, from which it passes through the opening 18 to flow into the gas compartment 15. In this process, the pyroelectric flow detector element 19 which is hotter than the gas G is cooled with the latter. Since the pyroelectric flow detector element 19 outputs signals in response to temperature change, signals indicated by a reference numeral 73 in FIG. 13C are output when the gas G flows.

When the infrared beam IR is no longer admitted into the gas compartments 14 and 15, the gas G is thermally in equilibrium; hence, the gas G that has flowed out of the gas compartment 14 into the gas compartment 15 moves backward, passing through the opening 18, gas channel 16, pyroelectric flow detector element 19 and opening 17 to return into the gas compartment 14. The return of the gas G is not abrupt enough to make a great contribution to the output signal level. Since the heater 28 is kept supplied with a constant voltage, the cooled pyroelectric flow detector element 19 is soon heated up, outputting signals as indicated by a reference numeral 74 in FIG. 13C.

We next describe the operation of the detector 9A shown in FIG. 7A which has two pyroelectric flow detector elements 19 and 19' placed one on top of the other.

III. First consider the case where only the heater 28' in the pyroelectric flow detector element 19' in the detector 9A is turned on to be held at a constant temperature. The following discussion should be read with reference to FIGS. 14A to 14F.

In the assumed case where only the pyroelectric flow detector element 19' is heated with the heater to be held at a constant temperature, if an infrared beam IR is launched into the gas compartments 14 and 15 (see FIG. 14A), the gas compartment 14 is the first to receive the admitted infrared beam IR. Hence, the gas in that compartment absorbs the infrared beam IR to become heated. On the other hand, the gas in the compartment 15 is little heated since the infrared beam IR has been absorbed by the gas in the compartment 14. In the assumed case, the two pyroelectric flow detector elements 19 and 19' present with the initial temperature profile shown in FIG. 14B.

Figure 14A:
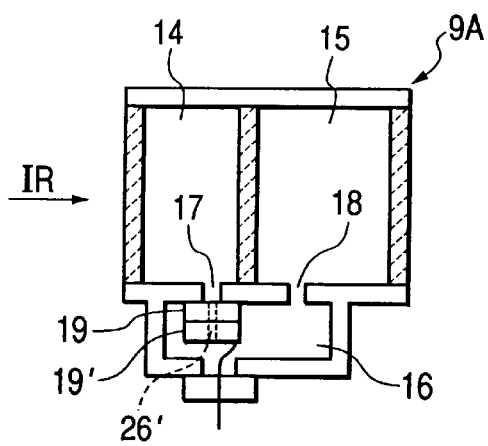
FIGS. 14A to 14F show in sequence how the detector shown in FIG. 7A operates when only one of the two pyroelectric flow detector elements is heated with a heater.
Figure 14B:
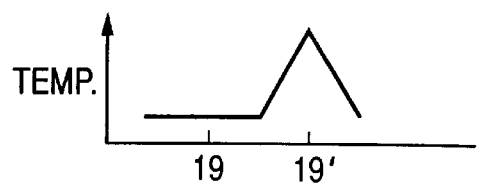
Figure 14C:
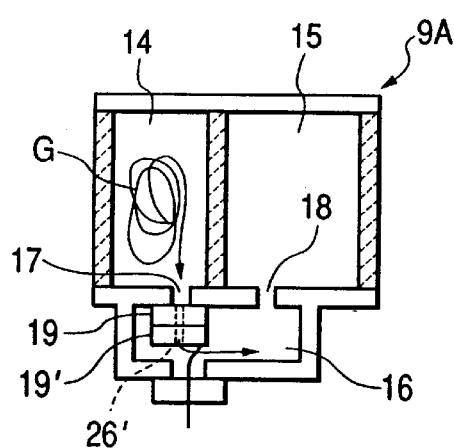
Figure 14D:
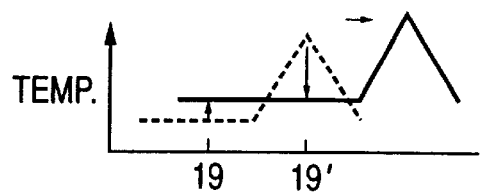
Figure 14E:
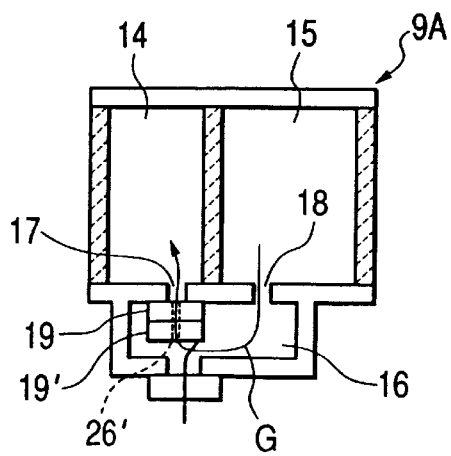
Figure 14F:
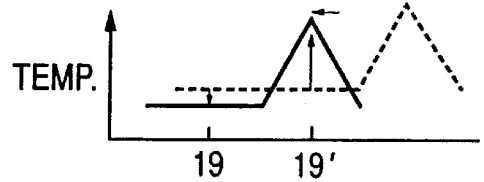

The heated gas G in the gas compartment 14 expands (see FIG. 14C) and passes through the opening 17 and the two pyroelectric flow detector elements 19 and 19' to enter the gas channel 16, from which it flows through the opening 18 into the gas compartment 15. In this process, the gas G heats up the pyroelectric flow detector element 19 which is not being heated with the heater whereas the pyroelectric flow detector element 19' is cooled down in spite of it being heated with the heater. Accordingly, the pyroelectric flow detector elements 19 and 19' present with the temperature profile indicated by a solid line in FIG. 14D. The arrows directed up and down in FIG. 14D represent the directions in which the temperatures of the pyroelectric flow detector elements 19 and 19' change. In the assumed case, the output signal level is the sum of the signals output in the above-described cases I and II.

When the infrared beam IR is no longer admitted into the gas compartments 14 and 15, the gas G is thermally in equilibrium; hence, the gas G that has flowed out of the gas compartment 14 into the gas compartment 15 moves backward, passing through the opening 18, gas channel 16, pyroelectric flow detector element 19 and opening 17 to return into the gas compartment 14. In this process, the temperature profile presented by the two pyroelectric flow detector elements 19 and 19' changes as indicated by a solid line FIG. 14F and the output signal level is the sum of the signals output in the above-described cases I and II.

IV. We next consider the case where the heaters 28 and 28' in the pyroelectric flow detector elements 19 and 19', respectively, in the detector 9A and turned on to be held at a constant temperature. The following discussion should be read with reference to FIGS. 15A to 15F.

In the assumed case where both pyroelectric flow detector elements 19 and 19' are heated with the heaters to be held at a constant temperature, if an infrared beam IR is launched into the gas compartments 14 and 15 (see FIG. 15A), the gas compartment 14 is the first to receive the admitted infrared beam IR. Hence, the gas in that compartment absorbs the infrared beam IR to become heated. On the other hand, the gas in the compartment 15 is little heated since the infrared beam IR has been absorbed by the gas in the compartment 14. In the assumed case, the two pyroelectric flow detector elements 19 and 19' present with the initial temperature profile shown in FIG. 15B.

Figure 15A:
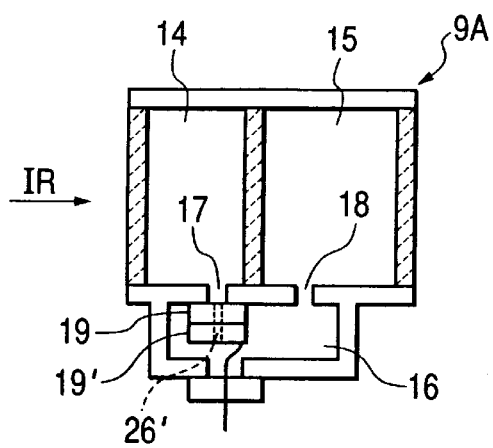
FIGS. 15A to 15F show in sequence how the detector shown in FIG. 7A operates when both pyroelectric flow detector elements are heated with a heater.
Figure 15B:
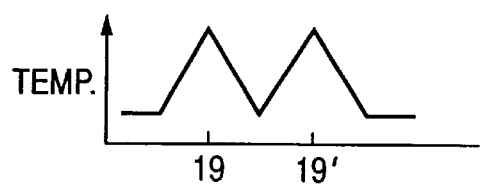
Figure 15C:
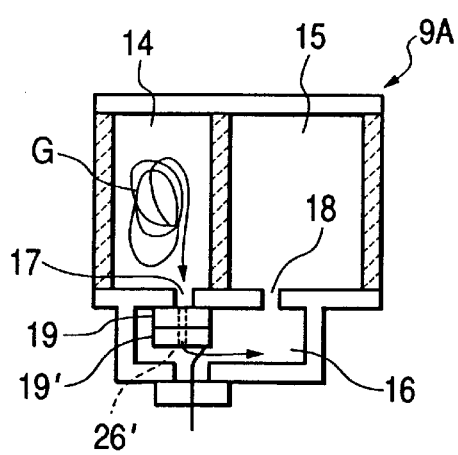
Figure 15D:
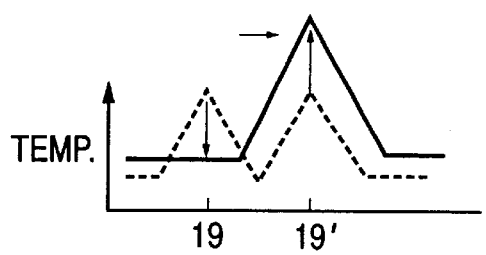
Figure 15E:
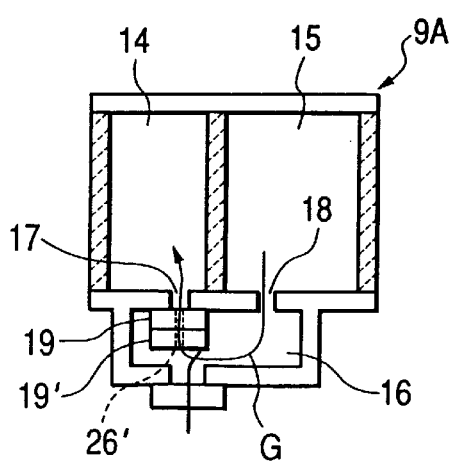
Figure 15F:
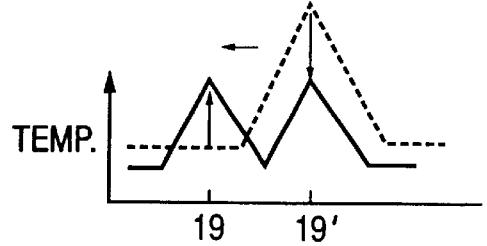

The heated gas G in the gas compartment 15 expands (see FIG. 15C) and passes through the opening 17 and the two pyroelectric flow detector elements 19 and 19' to enter the gas channel 16, from which it flows through the opening 18 into the gas compartment 15. In this process, the pyroelectric flow detector element 19 is cooled with the gas G but the other pyroelectric flow detector element 19' is further heated up by the gas G that has taken heat from the pyroelectric flow detector element 19. Therefore, the two pyroelectric flow detector elements 19 and 19' present with the temperature profile indicated by a solid line in FIG. 15D. The arrows directed up and down in FIG. 15D represent the directions in which the temperatures of the pyroelectric flow detector elements 19 and 19' change. In the assumed case, the output signal level is twice as much as is produced in the above-described case of II.

When the infrared beam IR is no longer admitted into the gas compartments 14 and 15, the gas G is thermally in equilibrium; hence, the gas G that has flowed out of the gas compartment 14 into the gas compartment 15 moves backward, passing through the opening 18, gas channel 16, pyroelectric flow detector elements 19 and 19, and opening 17 to return into the gas compartment 14. In this process, the temperature profile presented by the two pyroelectric flow detector elements 19 and 19' changes as indicated by a solid line in FIG. 15F and the output signal level is twice as much as is produced in the above-described case of II.

A word must be added to the assumed case where both pyroelectric flow detector elements 19 and 19' are heated with the heaters to be held at a constant temperature. If the temperatures of the two detector elements change in the same direction (i.e., both rise or fall), the resulting signals cancel each other to produce no output signal. In the above-described cases of III and IV, temperature changers occur in opposite directions (see FIGS. 14D and 15D) to produce output signals that are greater than in the other case.

To demonstrate the advantages of the invention, the pyroelectric flow detector element 19 used in it and a conventional thermal flow detector element were each assembled into an infrared gas analyzer of single-beam type shown in FIG. 3 and sensitivity measurements were conducted with sample gases being supplied. The results are described below as examples of the invention.

EXAMPLE 1

As shown in FIG. 3, one pyroelectric flow detector element 19 was assembled into the detector housing 10, with an appropriate concentration of CO gas being charged into the gas compartments 14 and 15 and the light chopper 8 operated at a frequency of 10 Hz. The performance of the pyroelectric detector element 19 was compared between two cases, without heating with the heater and with a dc voltage impressed on the heater up to 80° C. when Ar gas and 200 ppm of CO gas were flowed into the load cell 2, the results shown in Table 1 were obtained.

TABLE 1

| Sample gas | Thermal flow detector element | Pyroelectric flow detector element | |
|---|---|---|---|
| | | Heater off | Heated to 80° C. |
| Ar gas | 0.1 | 0.3 | 8.0 |
| CO gas | 0.085 | 0.255 | 6.8 |

As will be understood from Table 1, the detector of the invention which used the pyroelectric flow detector element 19 in the sensing portion had much higher sensitivities than the detector relying upon the conventional thermal flow detector element. The improvement was particularly great when the pyroelectric flow detector element 19 was heated with the heater. This is because the pyroelectric device is a differential detector element that depends on temperature difference for outputting signals.

EXAMPLE 2

As shown in FIG. 7A, two pyroelectric flow detector elements 19 and 19' were stacked and assembled into the detector housing 10. The other conditions were the same as in Example 1. When Ar gas and 200 ppm of CO gas were flowed into the load cell 2, the results shown in Table 2 were obtained.

TABLE 2

| Sample gas | Thermal flow detector element | Pyroelectric flow detector element | |
|---|---|---|---|
| | | Heater off | Heated to 80° C. |
| Ar gas | 0.1 | 0.3 | 13.0 |
| CO gas | 0.085 | 0.255 | 11.05 |

The detector of the invention which used pyroelectric flow detector elements in the sensing portion could produce greater signal outputs and higher detection sensitivities than the detector using the conventional thermal flow detector elements. Hence, the detector of the invention can advantageously be used with an infrared gas analyzer.

When the sensing portion of the pyroelectric flow detector element was heated, the features of the pyroelectric device as a differential detector element were exhibited more effectively to provide a marked improvement in detection sensitivity.

The use of two pyroelectric flow detector elements of identical construction was effective in suppressing the effects of ambient temperature and disturbances. In this case, a marked improvement could also be attained in detection sensitivity by heating the sensing portion of each pyroelectric flow detector element.

Figure 2:
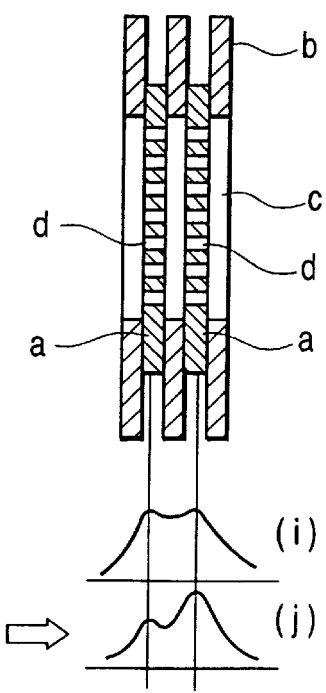
FIG. 2 is section Z—Z of FIG. 1.
Figure 16:
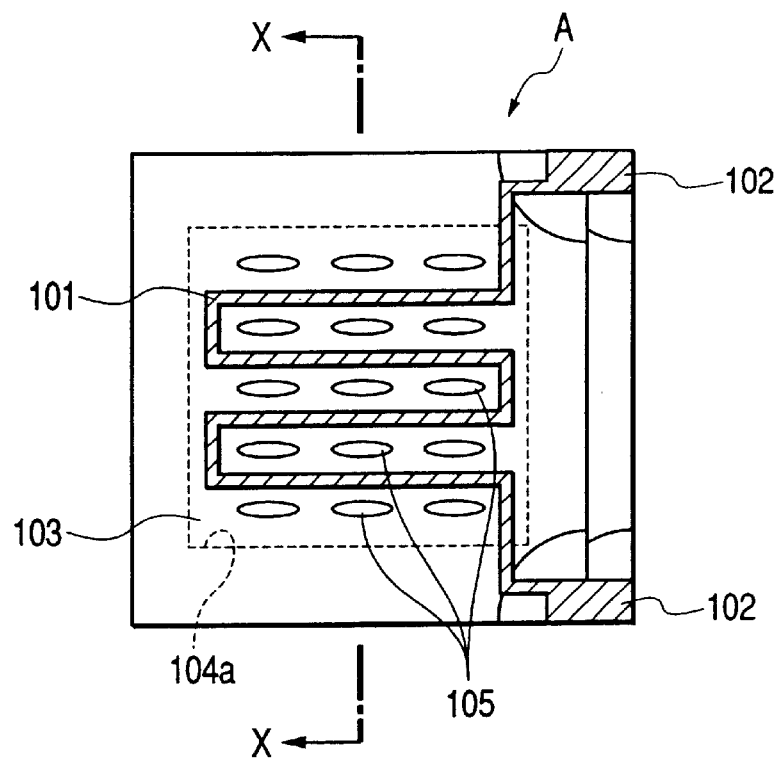
FIG. 16 is a plan view of a thermal flow detector element as an example of the flow detector element for use in infrared gas analyzers according to the invention.
Figure 17:
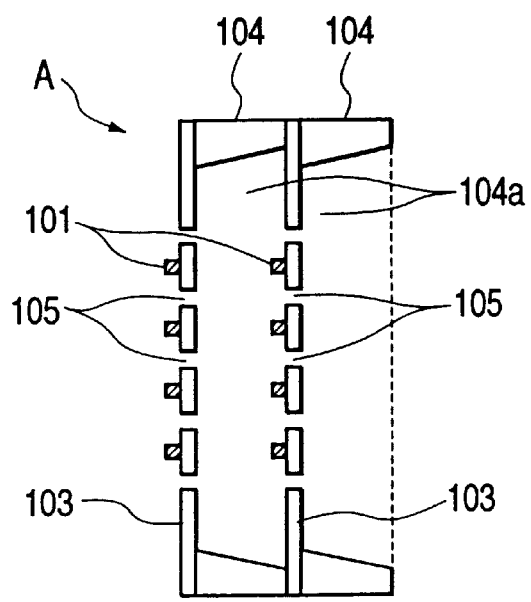
FIG. 17 is section X—X of FIG. 16.
Figure 18A:
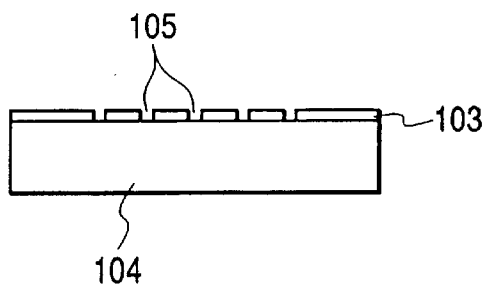
FIGS. 18A to 18E show the sequence of steps in a process for producing a thermal flow detector element.
Figure 18B:
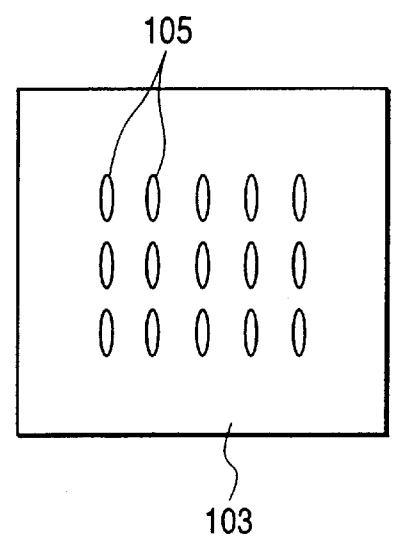
Figure 18C:
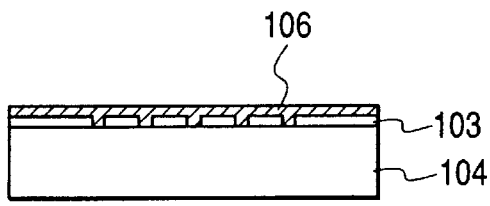
Figure 18D:
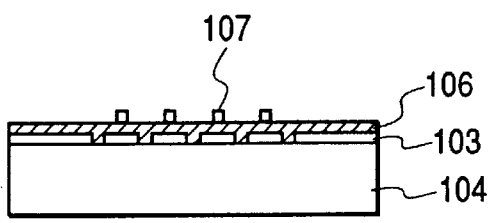
Figure 18E:
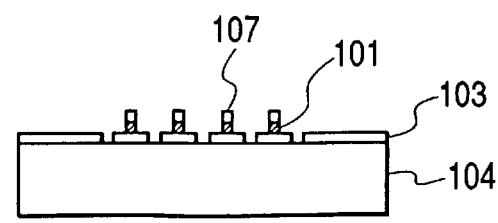
Figure 19A:
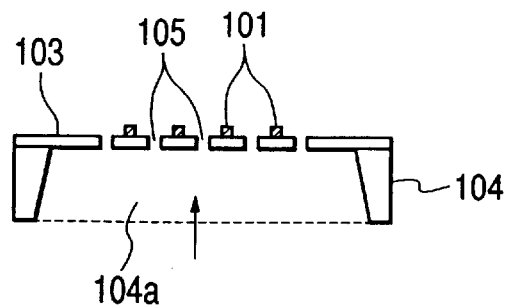
FIGS. 19A to 19C show the sequence of steps that follow FIG. 18E in completing the production of a thermal flow detector element.
Figure 19B:
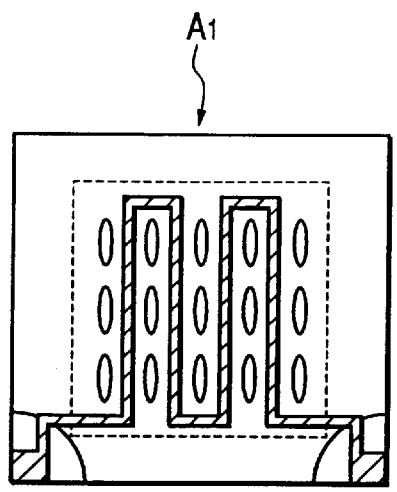
Figure 19C:
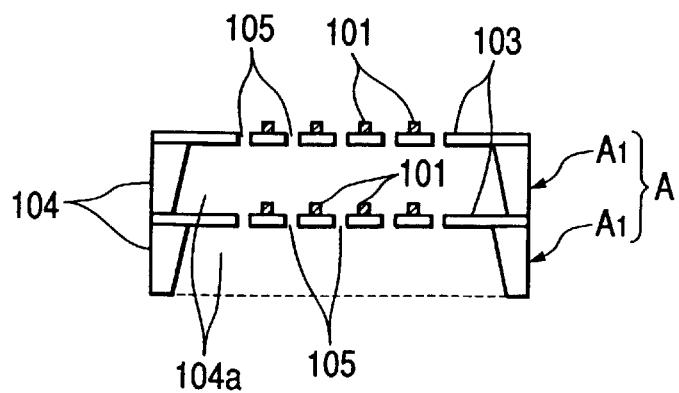

The flow detector element of the invention for use in infrared gas analyzers will now be described in greater detail with reference to FIGS. 16 to 24. The detector element is available in two types, thermal and pyroelectric. FIGS. 16 and 17 show a thermal flow detector element A which, like the conventional version shown in FIGS. 1 and 2, is provided in an obstructive way in a gas channel via which two gas compartments filled with a gas showing the same absorption characteristics as the gas to be measured communicate with each other. Indicated by 101 is a pair of heaters that are supplied with a constant voltage to have a temperature higher than that of the gas in the gas compartments by a certain value. The heaters 101 are formed in a serpentine pattern and impressed with electricity via conductors 102. The heaters are supported on thin insulator films 103.

The thin insulator films 103 may be made of either organic matter such as polyimide or epoxy compound or inorganic matter such as SiO2 or Si3N4. In the embodiment under discussion, the films 103 are made of a photosensitive polyimide. Indicated by 104 is a pair of substrate made of either amorphous glass or a crystalline material such as Si or MgO. An opening 104a is made in each substrate. Gas passage holes 105 having a channel area setting smaller than the area of the gap between adjacent segments of heater 101 are formed near the heaters 101 in that portion of each thin insulator film 3 which corresponds to the openings 104a. In the embodiment under consideration, a plurality of small oblong gas passage holes 105 having a smaller width than the distance between adjacent serpentine segments of heater 101 are formed along its path.

We now describe an exemplary process for producing the thermal flow detector element A with reference to FIGS. 18A to 19C. First, a substrate 104 made of amorphous glass or a crystalline material such as Si or MgO is overlaid with a thin insulator film 103 that is deposited from a photosensitive polyimide in a thickness of about 0.5 to 2 μm. Gas passage holes 105 are formed in specified positions in the thin insulator film 103 by a photoresist technique (see FIGS. 18A and 18B). The thin insulator film 103 is then overlaid with a heating electrode film (e.g. Pt, Ni or NiCr) 106 that is deposited in a thickness of about 0.1 to 0.3 μm by sputtering or other suitable technique (see FIG. 18C). After patterning by a photoresist technique (see FIG. 18D), the heating electrode film 106 is patterned by etching (see FIG. 18E). Indicated by 107 is the resist pattern. Then, the resist pattern 107 is stripped and the back side of the substrate 104 is selectively etched away to form an opening 104a, thereby making a unit of detector element Al (see FIGS. 19A and 19B). Thereafter, two units of detector element Al are stacked and bonded together (see FIG. 19C) to produce the thermal flow detector element A shown in FIG. 16.

According to the manufacturing process described above, the gas passage holes 105 can be formed without regard to the conductor size and pattern of the heaters 101 and by reducing the channel area of the gas passage holes 105, the gas flow rate can be sufficiently increased to provide higher sensitivity. In addition, the heaters 101 are supported by the thin insulator films 103, so there is no need to use a thick heating electrode film and the thermal flow detector element A can be formed as a thin enough film to reduce the heat capacity and thereby increase the response speed.

Figure 20:
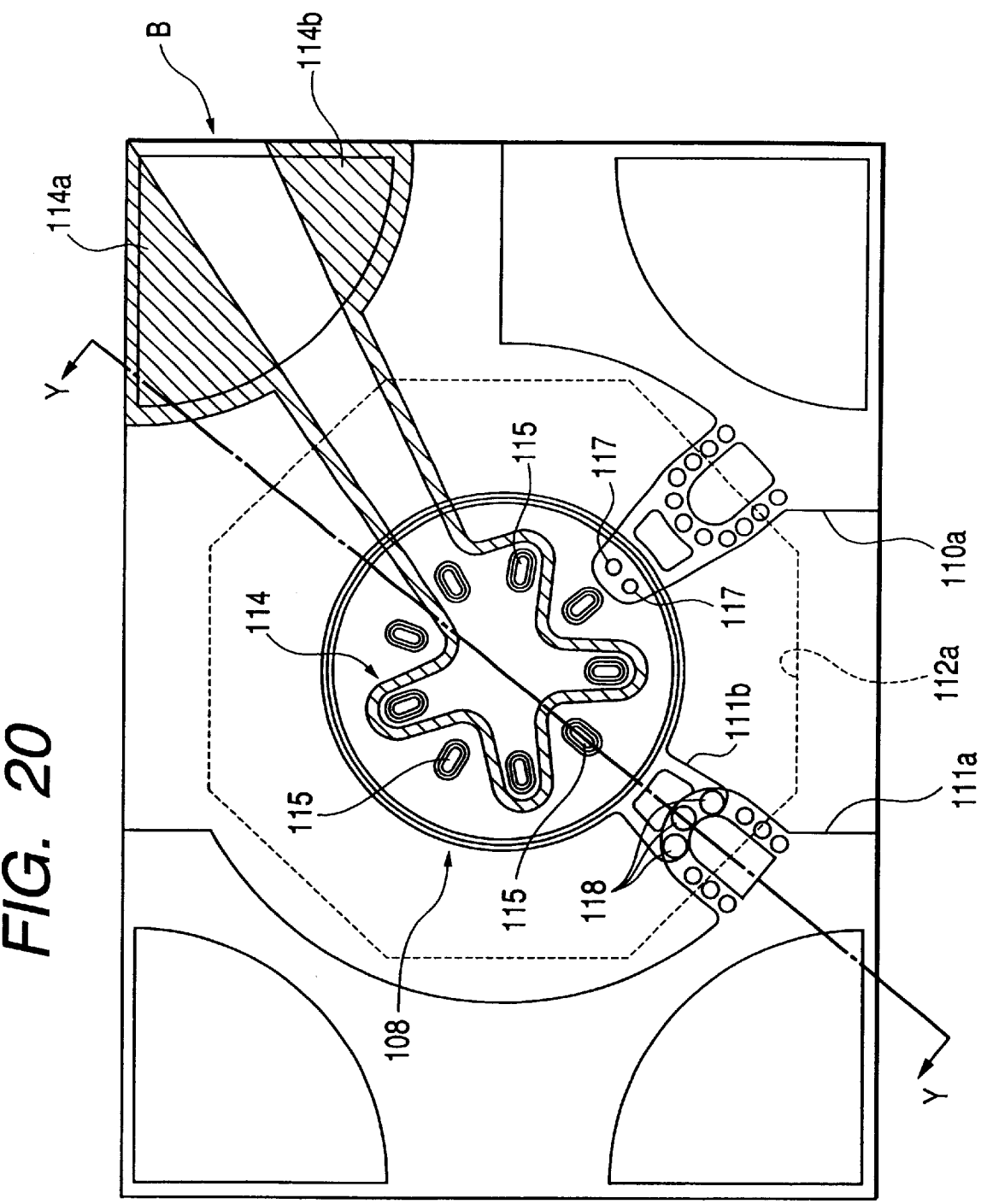
FIG. 20 is a plan view of a pyroelectric flow detector element as another example of the flow detector element of the invention for use in infrared gas analyzers.
Figure 22A:
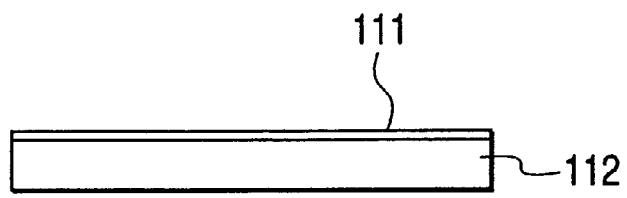
FIGS. 22A to 22C show the sequence of steps in a process for producing a pyroelectric flow detector element.
Figure 22B:
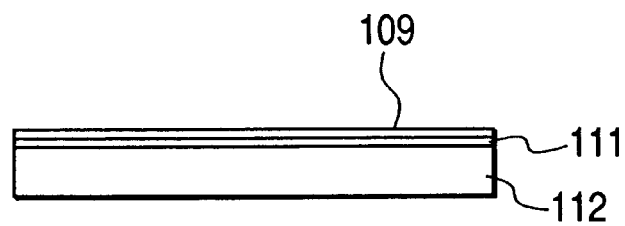
Figure 22C:
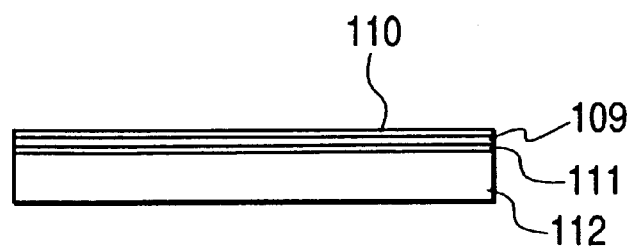
Figure 23A:
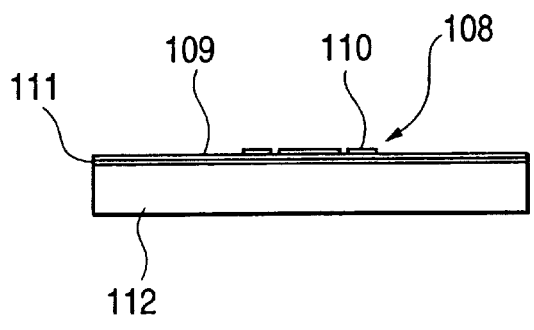
FIGS. 23A to 23D show the sequence of steps that follow FIG. 22C in producing a pyroelectric flow detector element.
Figure 23B:
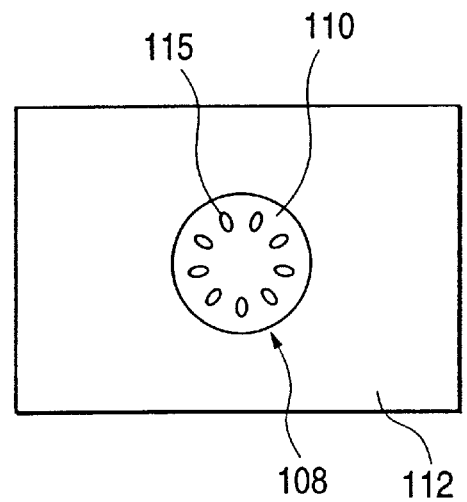
Figure 23C:
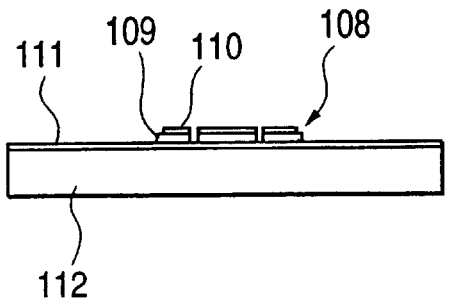
Figure 23D:
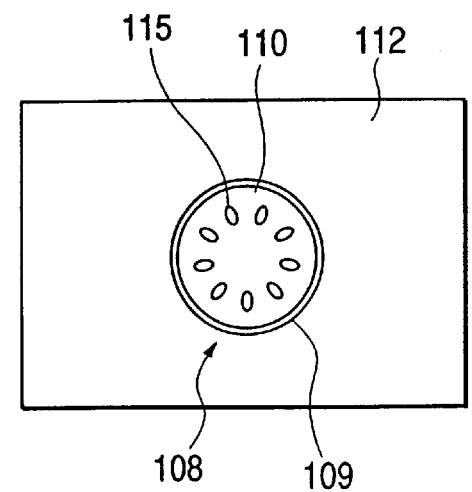

FIGS. 20, 21A and 21B show a pyroelectric flow detector element B which is the second type of the flow detector element of the invention for use in infrared gas analyzers. Like the already described thermal flow detector element A, the pyroelectric flow detector element B is provided in an obstructive way in a gas channel via which two gas compartments filled with a gas showing the same absorption characteristics as the gas to be measured communicate with each other.

Indicated by 108 is a pyroelectric sensing portion which consists of a thin ferroelectric (pyroelectric) film 109 sandwiched between an upper electrode 110 and a lower electrode 111. Indicated by 112 is a substrate made of single-crystal MgO or Si and which has an opening 112a.

A heater 114 is provided on top of the upper electrode 113, with a thin insulator film 113 interposed. The heater 114 is bent in a zigzag pattern to ensure the necessary length. The heater 114 is supplied with a constant voltage to have a temperature higher than that of the gas in the gas compartments by a certain value. The thin insulator film 113 may be formed of organic matter such as polyimide or epoxy compound or inorganic matter such as SiO2 or Si3N4; insulators having lower heat conductivities than metals are preferred.

Gas passage holes 115 of a small channel area that penetrate vertically through the substrate 112 are formed near the heater 114. In the illustrated case, nine such gas passage holes are formed equidistantly in the pyroelectric sensing portion 108. Indicated by 117 and 118 are contact holes; 110a is a lead-in for the upper electrode 110; 111a is a lead-in for the lower electrode 111; 114a and 114b are lead-in electrodes for the heater 114; 111b is a connection end of the lower electrode 111 which is connected to the lead-in 111a within the contact holes 118. The pyroelectric sensing portion 108 and the heater 114 are located above the opening 112a in the substrate 112 but supported on the latter via the thin insulator film 113.

To operate the pyroelectric flow detector element B, the heater 114 is supplied with a constant voltage so that it is heated to a constant temperature, say, 80 to 110° C. If there is no gas flow, the output from the pyroelectric sensing portion 108 is zero. In the presence of a gas flow, the heater 114 is cooled in accordance with the flow rate of the gas passing through the holes 115, causing a temperature change in the pyroelectric sensing portion 108, which then outputs signals indicative of the temperature change, hence, the gas flow. The detected gas flow enables determination of the quantity of infrared absorption by the gas of interest (hence its concentration) that is passed through the load cell (not shown) in a nondispersive infrared gas analyzer.

We now describe an exemplary process for producing the pyroelectric f low detector element B with reference to FIGS. 22A to 24F. The substrate 112 which is made of single-crystal MgO or Si is sputtered or otherwise treated to be overlaid with a Pt layer in a thickness of about 0.2 μm so that it works as the lower electrode 111 (see FIG. 22A). The lower electrode 111 is treated by MOCVD (metalorganic chemical vapor deposition) or otherwise to be overlaid with a thin PZT or PLZT ferroelectric film 109 in a thickness of about 2 to 5 μm (see FIG. 22B). The thin ferroelectric film 109 is sputtered or otherwise treated to be overlaid with a Au or Pt layer in a thickness of about 0.2 μm so that it works as the upper electrode 110 (see FIG. 22C). The upper electrode 110, the thin ferroelectric film 109 and the lower electrode 111 are sequentially patterned by photolithography (see FIGS. 23A to 23D, and 24A and 24B). As the result of patterning, through-holes which later serve as the gas passage holes 115 are formed.

Figure 24A:
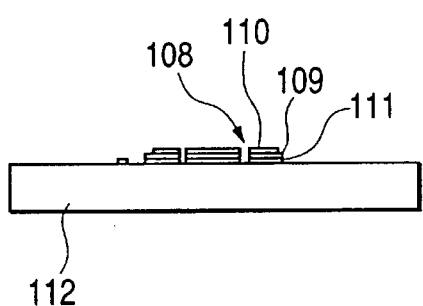
FIGS. 24A to 24F show the sequence of steps that follow FIG. 23D in completing the production of a pyroelectric flow detector element.
Figure 24B:
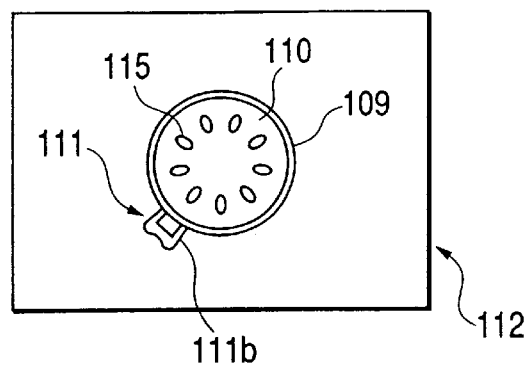
Figure 24C:
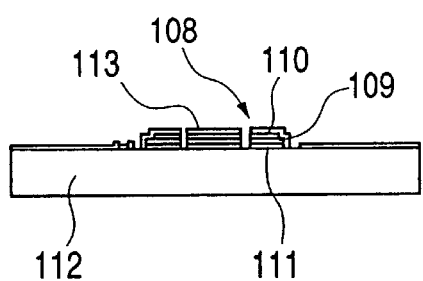
Figure 24D:
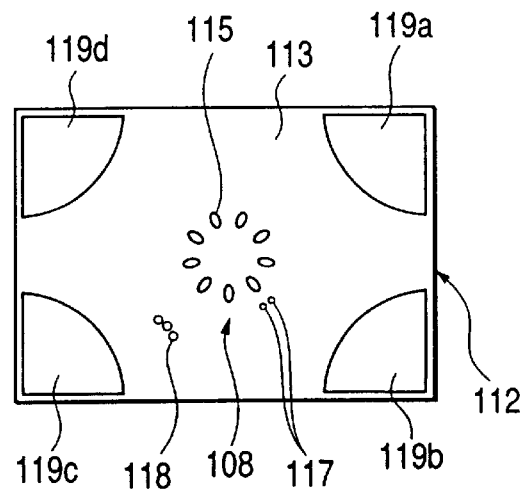
Figure 24E:
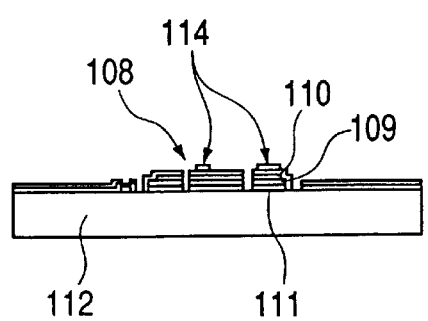
Figure 24F:
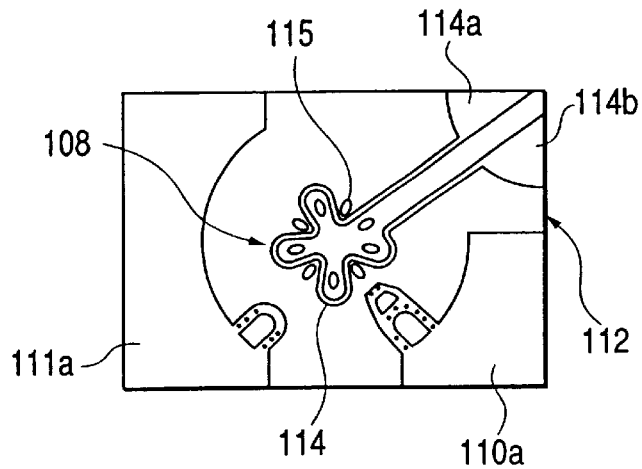

The pyroelectric sensing portion 8 is covered with a thin insulator film 113 (see FIGS. 24C and 24D). As shown specifically in FIG. 24D, the thin insulator film 113 has not only through-holes that later serve as the gas passage holes 115 but also the contact holes 117 and 118, and recesses 119a, 119b, 119c and 119d that serve as the base of lead-in electrodes. The thin insulator film 113 is overlaid with a heating electrode film (typically from Pt or NiCr) that later serves as the heater 114. The heating electrode film is then patterned by photolithography, with part of the Pt or NiCr being allowed to drop in the contact holes 117 and 118 so as to form the lead-in 110a for the upper electrode and the lead-in 111a for the lower electrode (see FIGS. 24E and 24F). In the illustrated case, the lead-ins for the upper and lower electrodes are formed simultaneously with the heating electrode film; however, this is not the sole case of the invention and those lead-ins may be formed in a separate step from the heating electrode film. Subsequently, that part of the substrate 112 which is just under the pyroelectric sensing portion 108 is etched away to form the opening 112a so that the gas passage holes 115 penetrate vertically through the substrate 112. This completes the production of the pyroelectric flow detector element B.

The pyroelectric flow detector element B inherently has a higher sensitivity and response speed than the thermal flow detector element A. According to the manufacturing process described above, this advantage of the pyroelectric flow detector element B can be furthered. Stated more specifically, the gas passage holes 115 can be formed without regard to the conductor size and pattern of the heater 114 and by reducing the channel or flow path area of the gas passage holes 115, the gas flow rate can be sufficiently increased to provide higher sensitivity. In addition, the thin ferroelectric film 109 is very thin (ca. 2 to 5 μm) and the heater 114 is supported by the thin insulator film 113, so there is no need to use a thick heating electrode film. As the result of these features, the pyroelectric flow detector element B can be formed as a thin enough film to reduce the heat capacity and thereby increase the response speed.

In short, the present invention has the advantage of increasing the sensitivity and response speed of a flow detector element for use in infrared gas analyzers.

What is claimed is:

1. A detector for use in infrared gas analyzers comprising:
   two gas compartments to be filled with a gas showing the same absorption characteristics as the gas to be measured and which are arranged in series with a load cell;
   a gas channel via which the two gas compartments communicate with each other;
   a first pyroelectric flow detector element disposed in said gas channel.

2. A detector for use in infrared gas analyzers comprising:
   two gas compartments to be filled with a gas showing the same absorption characteristics as the gas to be measured and which are arranged in parallel so that they correspond to a load cell and a reference cell, respectively;
   a gas channel via which the two gas compartments communicate with each other;
   a first pyroelectric flow detector element disposed in said gas channel.

3. The detector for use in infrared gas analyzers according to claim 1, further comprising a heater for heating sensing portion of said first pyroelectric flow detector.

4. The detector for use in infrared gas analyzers according to claim 2, further comprising a heater for heating sensing portion of said first pyroelectric flow detector.

5. The detector for use in infrared gas analyzers according to claim 1, further comprising second pyroelectric flow detector element being provided as a compensating means in the neighborhood of said first pyroelectric flow detector element.

6. The detector for use in infrared gas analyzers according to claim 2, further comprising second pyroelectric flow detector element being provided as a compensating means in the neighborhood of said first pyroelectric flow detector element.

7. The detector for use in infrared gas analyzers according to claim 1, further comprising second pyroelectric flow detector element superposed on said first pyroelectric flow detector element as a compensating means.

8. The detector for use in infrared gas analyzers according to claim 2, further comprising second pyroelectric flow detector element superposed on said first pyroelectric flow detector element as a compensating means.

9. The detector for use in infrared gas analyzers according to any one of claims 4 to 8, further comprising a heater for heating sensing portion of at least one of said first and second pyroelectric flow detectors.

10. A flow detector element in a detector for use in infrared gas analyzers:
    two gas compartments filled with a gas showing the same absorption characteristics as the gas to be measured;
    a gas channel via which the two gas compartments communicate with each other;
    a flow detector element provided in said gas channel;
    a heater to be supplied with a constant voltage so that its temperature is a certain value higher than the temperature of the gas in the gas compartments; and
    a gas passage hole being formed in the neighborhood of said heater, the channel area of said gas passage hole being smaller than the area of the gap between adjacent segments of the heater.

11. The flow detector element in a detector for use in infrared gas analyzers according to claim 10, which is of a thermal type.

12. The flow detector element in a detector for use in infrared gas analyzers according to claim 10, which is of a pyroelectric type.

* * * * *